United States Patent [19]

Wittwer et al.

[11] Patent Number: 4,655,840
[45] Date of Patent: Apr. 7, 1987

[54] HYDROPHILIC POLYMER COMPOSITIONS FOR INJECTION MOLDING

[75] Inventors: Fritz Wittwer, Lupsingen; Ivan Tomka, Zollikon, both of Switzerland

[73] Assignee: Warner-Lambert Company, Morris Plains, N.J.

[21] Appl. No.: 698,264

[22] Filed: Feb. 5, 1985

Related U.S. Application Data

[63] Continuation-in-part of Ser. No. 362,177, Mar. 26, 1982, abandoned.

[51] Int. Cl.$^4$ .................. C09D 3/04; C08L 89/00; B29B 7/00
[52] U.S. Cl. ........................... 106/126; 106/125; 106/127; 106/128; 106/129; 106/130; 106/136; 524/22; 524/23; 264/328.1
[58] Field of Search ............... 260/118, 117; 106/184, 106/197.1, 197.2, 125–130, 136; 536/91; 524/22, 23; 264/297.2, 328.1

[56] References Cited

U.S. PATENT DOCUMENTS

| | | | |
|---|---|---|---|
| 2,602,755 | 7/1952 | Silvernail | 536/91 |
| 3,137,592 | 6/1964 | Protzman et al. | 127/32 |
| 3,321,313 | 5/1967 | Burness | 96/111 |
| 3,520,971 | 7/1970 | Benford | 424/37 |
| 3,653,934 | 4/1972 | Rolle | 106/125 |
| 3,758,660 | 9/1973 | Battista | 264/202 |
| 3,765,917 | 10/1973 | Hijiya | 106/126 |
| 3,826,666 | 7/1974 | Hirai | 106/128 |
| 3,865,603 | 2/1975 | Szymanski | 106/130 |
| 4,010,038 | 3/1977 | Iwasaki | 106/22 |
| 4,045,239 | 8/1977 | Hammer | 106/147 |
| 4,076,846 | 2/1978 | Nakatsuka | 426/248 |
| 4,138,013 | 2/1979 | Okajima | 206/528 |
| 4,224,348 | 7/1980 | Hayashi | 426/234 |
| 4,264,493 | 4/1981 | Battista | 260/117 |
| 4,352,695 | 10/1981 | Tomka | 106/135 |
| 4,369,069 | 1/1983 | Graesser | 260/118 |
| 4,482,386 | 11/1984 | Wittwer et al. | 260/117 |
| 4,591,475 | 5/1986 | Tomka | 424/37 |

FOREIGN PATENT DOCUMENTS 1965584 7/1970 Fed. Rep. of Germany .
1230759 4/1960 France .
2307523 11/1976 France .

OTHER PUBLICATIONS

Glafkides, P. "Chimie et physique Photographiques", 3d ed., 1967, pp. 222, 300, 326–328.
Greminger and Savage, Industrial Gums, 2d ed., Whistler (Ed.), 1973, p. 642.
Kozlov and Burdygina, Polymer 24:651 (1983).
Pauli and Valko, "Colloid Chemistry of Proteins", in Handbuch Der Kolloid wissenschaft, Ostwald (Ed), 1933, p. 254 (Table 75), p. 257.
Ullmann, Encylopedie der technischen Chemie, 4th Ed., vol. 12, "Fungizide bis Holzwerstoffe", 1976, pp. 213–214.

Primary Examiner—Theodore Morris
Attorney, Agent, or Firm—Howard Olevsky; Stephen Raines

[57] ABSTRACT

A moldable hydrophilic polymer composition, preferably gelatin, for use in an injection molding device preferably controlled with a microprocessor. The composition has a molecular mass range of 10,000 to 2,000,000 Dalton or a molecular mass range of 10,000 to 2,000,000 and 10,000,000 to 20,000,000 Dalton. The composition has a water content range from 5 to 25% percent by weight.

17 Claims, 11 Drawing Figures

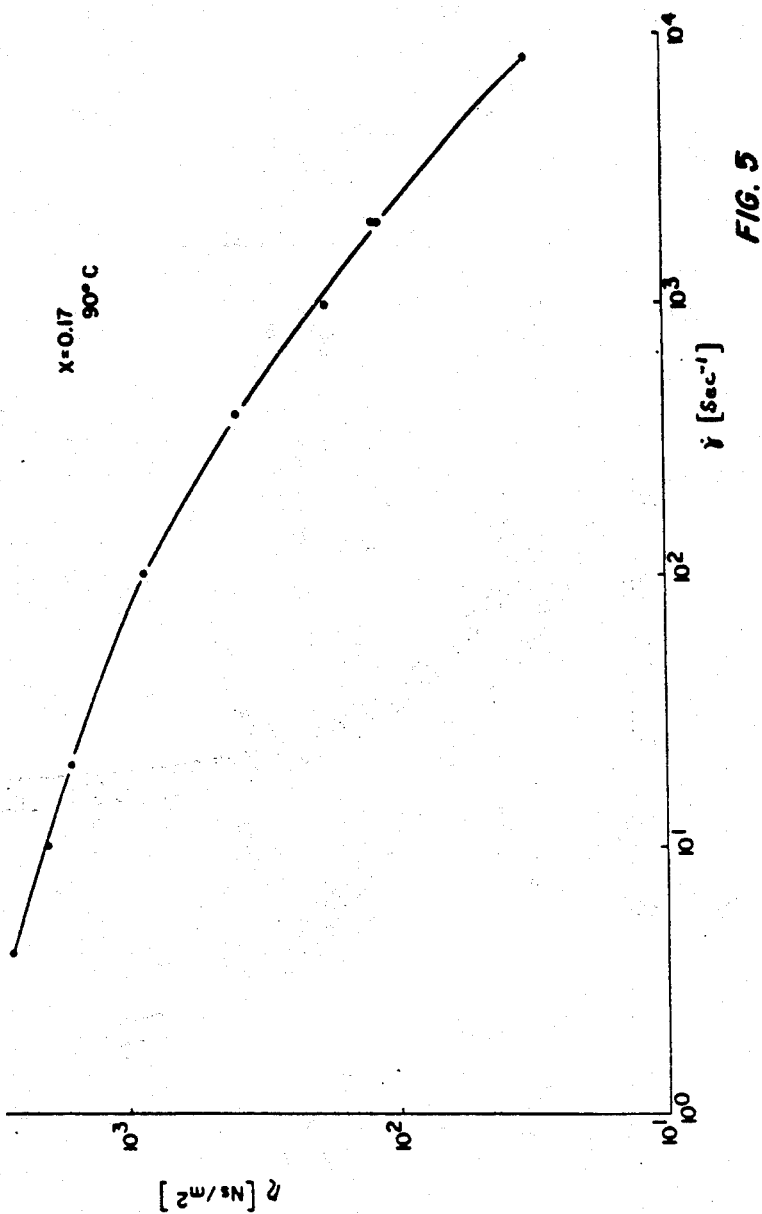

HYDROPHILIC POLYMER COMPOSITIONS FOR INJECTION MOLDING

This is a continuation in part of patent application U.S. Ser. No. 362,177 filed Mar. 26, 1982 now abandoned.

BACKGROUND OF THE INVENTION

Field of the Invention

The present invention relates to a moldable hydrophilic polymer composition, preferably gelatin, for use in an injection molding device preferably with a microprocessor, to produce capsules. The present invention utilizes gelatin made from various types of gelatin, including acid or alkaline processed ossein, acid processed pigskin, or alkaline processed cattle hide. Said types of gelatin have a molecular mass range of 10,000 to 2,000,000 Dalton or a molecular mass range of 10,000 to 2,000,000 and 10,000,000 to 20,000,000 Dalton. The method for determination of the molecular mass distribution of the various types of gelatin used in the present invention is described in the following references:

I. Tomka, Chimia. 30, 534–540 (1976)
I. Tomka, et al, Phot. Sci. 23, 97 (1975)

Gelatin having a molecular mass range between 10,000 and 2,000,000 Dalton, was found to give less deformation of capsule parts after ejection from a capsule mold, When in the following description the term "gelatin" is used, other hydrophilic polymer compositions whose properties are acceptable as capsule materials are also included. Hydrophilic polymers are polymers with molecular masses from approximately $10^3$ to $10^7$ Dalton carrying molecular groups in their backbone and/or in their side chains and capable of forming and/or participating in hydrogen bridges. Such hydrophilic polymers exhibit in their water adsorption isotherm (in the temperature range between approximately 0° to 200° C.) an inflection point close to the water activity point at 0.5. Hydrophilic polymers are distinguished from the group called hydrocolloids by their molecular dispersity. For the maintenance of the molecular dispersity of said hydrophilic polymers a fraction of water—according to the working range of the present invention—of 5 to 25% by weight of said hydrophilic polymers must be included provided that the temperature of said hydrophilic polymers is in the working range between 50° C. and 190° C. of the present invention.

There are other hydrocolloids, not hydrophilic polymers in the sense of this definition, which contain more or less spherical or fibrous particles whereby those particles are composed of several macromolecules of a hydrophilic polymer within the molecular mass range of $10^3$–$10^7$ Dalton giving rise to particle sizes between 0.01–10 microns which is the typical range of colloidal particles. It is a primary object of the present invention to utilize hydrophilic polymer compositions in the production of capsules.

REFERENCES TO COPENDING PATENT APPLICATIONS

Concurrently with this application please also refer to patent application U.S. Ser. No. 490,057 filed Apr. 29, 1983, now U.S. Pat. No. 4,591,475 and to patent application U.S. Ser. No. 362,430 filed Mar. 26, 1982, now abandoned, both of which are copending with this application.

Description of the Prior Art

Capsule-making machines have been developed to utilize dip-molding technology. Such technology involves the dipping of capsule-shaped pins into a gelatin solution, removing the pins from the solution, drying of the gelatin upon the pins, stripping off the gelatin capsule parts from the pins, adjusting for length, cutting, joining and ejecting the capsules. Prior art capsule-making machines have utilized the combination of mechanical and pneumatic elements to perform these functions at speeds up to about 1,200 size 0 capsules per minute. While the above described apparatus are in general suitable for the intended purposes, it is desirable to produce capsules at considerably higher speed, over 15,000 size 0 capsules per minute, while at the same time precisely controlling the properties of the gelatin in order to produce the capsules hygienically and with minimum dimensional deviations so that the capsules can be filled on high speed equipment.

A prerequisite for any material to be moldable by an injection process is its ability to pass a glass transition point at a temperature compatible with the thermal stability of the material and the technical possibilities of an injection molding device.

Shirai et al. in U.S. Pat. Ser. No. 4,216,240 describes an injection molding process to produce an oriented fibrous protein product. The fibrous product as obtained by this process differs fundamentally from the transparent glasslike material of the capsules obtained from the present invention. Furthermore to obtain a flowable mass for the molding process, the protein mixtures used by Shirai et al. have to be denatured and thus lose their capacity to undergo dissolution.

Nakatsuka et al. in U.S. Pat. No. 4,076,846 uses binary mixtures of starch with salts of protein materials to obtain an edible shaped article by an injection molding process. With the present invention shaped articles from protein materials, preferably gelatin and other hydrophilic polymers can be produced without the addition of starch.

Heusdens et al. in U.S. Pat. No. 3,911,159 discloses the formation of filamentous protein structures to obtain edible products of improved tenderness. With the present invention shaped articles are produced without a filamentous protein structure.

The use of an injection molding device for producing capsules of gelatin and other moldable hydrophilic polymers with similar properties is new and has not been suggested in the technical literature.

The present invention distinguishes from the known as described above, by the nature of the compositions and by the recognition that gelatin and other hydrophilic polymers possess a dissolution point within a temperature range usable for an injection molding process, provided the water content of the gelatin and other hydrophilic polymers lies within a characteristic range, giving allowance to avoid any essential drying or humidification processes of the capsules.

SUMMARY OF THE INVENTION

The present invention covers an improved hydrophilic polymer composition, preferably gelatin, for use in an improved automatic injection molding device combined with a microprocessor to control the optimum time, temperature, pressure and water content of the composition in formed shaped parts. The composition has a molecular mass range of 10,000 to 2,000,000 Dalton or a molecular mass range 10,000 to 2,000,000 and 10,000,000 to 20,000,000 Dalton.

The composition has a water content range of approximately 5 to 25% by weight.

It is therefore a primary object of the present invention to provide a new and improved moldable composition of hydrophilic polymers for use with an injection molding-microprocessor apparatus which alleviates one or more of the above described disadvantages of the prior art compositions.

It is another object of the present invention to provide a new and improved moldable composition of hydrophilic polymers for use with an injection molding-microprocessor apparatus in method of molding capsules by continuous monitoring and control of the pertinent parameters in order to prevent degradation of the moldable composition of hydrophilic polymers and deformation of the capsules.

It is a further object of the present invention to provide a moldable composition of hydrophilic polymers for use with an injection molding-microprocessor apparatus in a method of molding capsules at high speed and with precision in order to use the capsules with high speed filling equipment.

BRIEF DESCRIPTION OF THE DRAWINGS

The invention both as to its organization and method of operation together with further objects and advantages thereof will best be understood by reference to the following specifications and taken in conjunction with the accompanying drawings.

FIG. 5 is the diagram of dependence of shear viscosity of gelatin within the pertinent ranges of the shear rate in the present invention;

DETAILED DESCRIPTION OF THE PREFERRED EMBODIMENT

Figure 1:
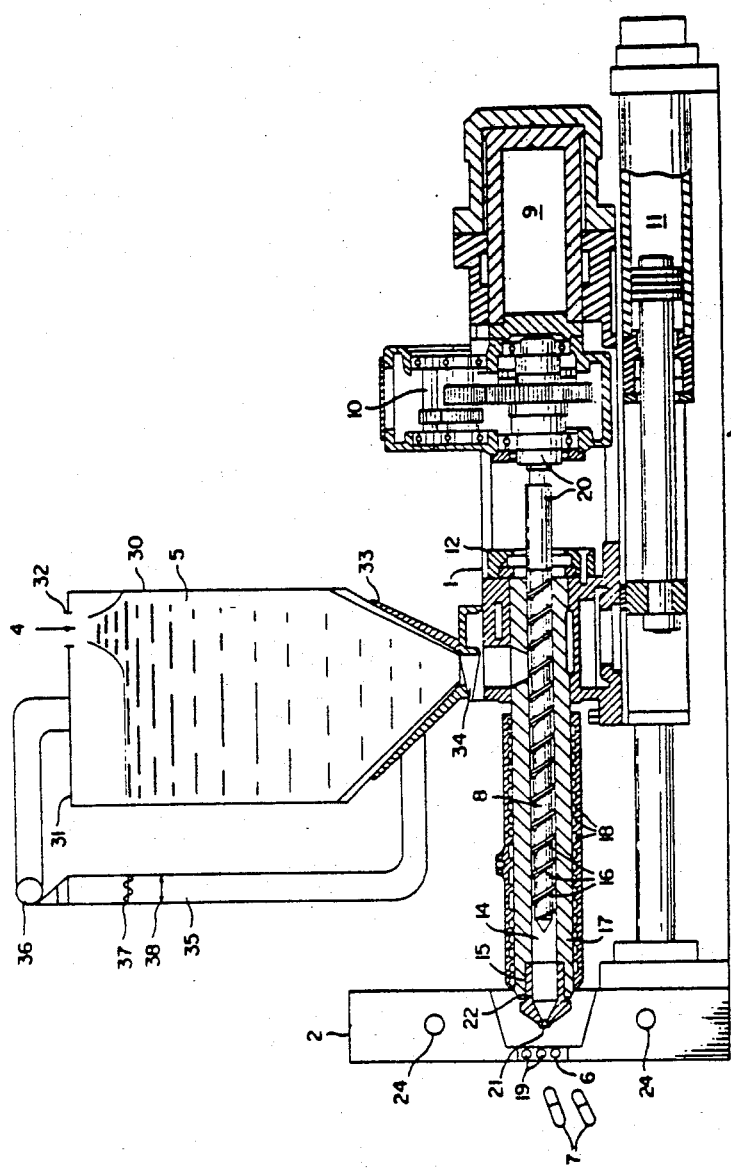
FIG. 1 is a layout of the reciprocating screw injection molding device for making capsule parts.

Referring now to FIG. 1 the injection molding device 27 generally consists of three units: a hopper unit 5, an injection unit 1 and a molding unit 2.

The function of the hopper unit 5 is receiving, storing, maintaining and feeding gelatin 4 at a constant temperature and at a constant water content. The hopper unit 5 comprises a vertical cylinder 30 having a closed top 31 with an inlet 32 therein to receive gelatin 4. At the bottom of the vertical cylinder 30 is a closed conical funnel 33 and a discharge outlet 34 to feed gelatin 4 into an inlet 34 of the injection unit 1. There is an air duct 35 communicating between the closed top 31 and the conical funnel 33 wherein air is circulated by a blower 36, the air temperature is maintained by a thyristor 37 and the air relative humidity is maintained by a steam injector 38.

The function of the injection unit 1 is melting, dissolving in water, and plasticizing in the extruder barrel 17 the gelatin 4 fed from the hopper unit 5 into the extruder inlet 54 and injecting the plasticized gelatin 14 into the molding unit 2.

The function of the molding unit 2 is automatically holding, opening and closing the mold 6 having capsule shaped cavities 19 therein, and ejecting the capsule parts 7 therefrom.

Within the injection unit 1 the screw 8 both rotates and undergoes axial reciprocal motion. When the screw 8 rotates, it performs the functions of melting, dissolving in water, and plasticizing the gelatin 4. When the screw 8 moves axially, it performs the function of injecting by transporting and ramming the plasticized gelatin 14 into the mold 6. The screw 8 is rotated by a variable-speed hydraulic motor and drive 10, and its axial motion is reciprocated by a duplex hydraulic cylinder 9.

Compression of the plasticized gelatin 14 in front of the rotating screw 8 forces back the screw assembly 20 containing the screw 8, the drive 10 and the cylinder 9. When the screw assembly 20 reaches a pre-setback position a limit switch 12 is contacted. When a defined time has elapsed during which the gelatin 4 becomes fully plasticized gelatin 14 the hydraulic cylinder 11 brings the screw assembly 20 forward and uses the screw 8 as a ram for the plasticized gelatin 14 to be injected through a valve body assembly 50 (FIG. 4) including a one-way valve 15, a needle valve 23, nozzle 22 and an outlet port 21 into the molding unit 2. The one-way valve 15 prevents the plasticized gelatin 14 from going back over the helical flutes 16 of the screw 8. The extruder barrel 17 has steam heating coils 18 to heat the gelatin 4 while it is being compressed by the screw 8 into plasticized gelatin 14. It is desirable for the plasticized gelatin 14 to be heated at the lowest possible temperature and to be transported with the lowest possible speed of the screw 8. The speed of the screw 8 and the heating of the plasticized gelatin 14 within the extruder barrel 17 by the steam heating coils 18 control the quality and the output rate of the plasticized gelatin 14 injected into the molding unit 2. The molding unit 2 holds the mold 6 having capsule shaped cavities 19 into which the plasticized gelatin 14 is injected and maintained under pressure. Refrigerant cooling conduits 24 encircle the mold 6 so that when the plasticized gelatin 14 in the mold 6 has cooled and sufficiently solidified, the molding unit 2 opens, the mold 6 separates and the capsule parts 7 are ejected.

Figure 2:
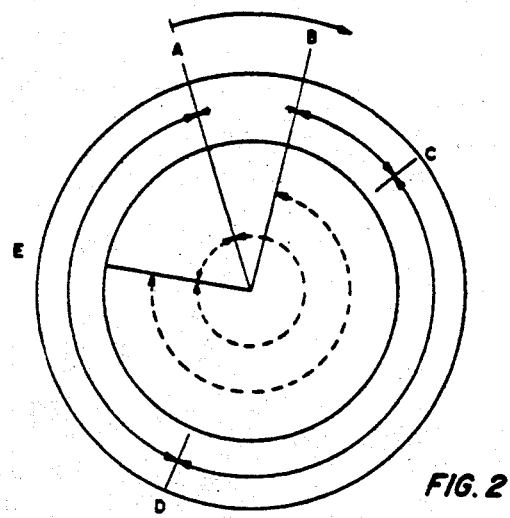
FIG. 2 is a schematic of the injection molding work cycle for making capsule parts.

Referring now to FIG. 1 and also to FIG. 2 which depicts the injection molding work cycle for gelatin 4 (containing approximately 17% water by weight) plotted against time. In general the work cycle of gelatin 4 is as follows in the injection molding device 27 of the present invention:

a. gelatin 4 is fed into the hopper unit 5 where it is received, stored and maintained under conditions of temperature ranging from ambient to 100° C., pressure ranging from $1-5 \times 10^5$ Newtons per square meter ($N \times m^{-2}$) and water content ranging from 5 to 25% by weight of gelatin, b. the stored gelatin is melted under controlled condition of temperature ranging from 50° to 190° C., water content ranging from 5 to 25% by weight of gelatin and pressure ranging from 600 to $3000 \times 10^5$ $N \times m^{-2}$, c. the molten gelatin is dissolved in water under controlled conditions of temperature ranging from 50° to 190° C. pressures ranging from 600 to $3000 \times 10^5$ $N \times m^{-2}$, and water content ranging from 5 to 25% by weight of gelatin.

d. the dissolved gelatin is plasticized under controlled conditions of temperature ranging from 50° to 190° C., pressure ranging from from 600 to $3000 \times 10^5$ $N \times m^{-2}$ and water content ranging from 5 to 25% by weight of gelatin.

e. the plasticized gelatin is injected into the mold 6 under controlled conditions of temperature below 50° C., injection pressure ranging from 600 to $3000 \times 10^5$ $N \times m^{-2}$ and a clamping force of the mold 6 below approximately 600,000 Newton, and f. the capsule-shaped parts 7 are ejected from the molded gelatin within the mold 6.

Beginning at point A of FIG. 2 the screw 8 moves forward and fills the mold 6 with plasticized gelatin 14 until Point B and maintains the injected plasticized gelatin 14 under high pressure, during what is called the hold time from point B until Point C of FIG. 2. At Point A the one-way valve 15 at the end of the screw 8 prevents the plasticized gelatin 14 from flowing back from the nozzle 22 onto the screw 8. During hold time, additional plasticized gelatin 14 is injected, offsetting contraction due to cooling and solidification of the plasticized gelatin 14. Later, the outlet port 21, which is a narrow entrance to the molding unit 2 closes, thus isolating the molding unit 2 from the injection unit 1. The plasticized gelatin 14 within the mold 6 is still at high pressure. As the plasticized gelatin 14 cools and solidifies, pressure drops to a level that is high enough to ensure the absence of sinkmarks, but not so high that it becomes difficult to remove the capsule parts 7 from the capsule-shaped cavities 19 within the mold 6. After the outlet port 21 closes, at Point C, screw 8 rotation commences. The plasticized gelatin 14 is accommodated in the increased cylindrical space in front of the screw 8 created by its backward axial motion until Point D. The flow rate of the plasticized gelatin 14 is controlled by the speed of the screw 8 and the pressure is controlled by the back pressure (i.e., the hydraulic pressure exerted on the screw assembly 20) which in turn determines the pressure of the plasticized gelatin 14 at the nozzle 22 in front of the screw 8. After plasticized gelatin 14 generation for the next shot into the mold 6, the screw 8 rotation ceases at Point D. The gelatin 4 on the stationary screw 8 continues to melt from Points D to E by heat conduction from the steam heating coils 18 on the extruder barrel 17. This period is called soak time. Meanwhile, the solidified capsule parts 7 are ejected from the mold 6. Thereafter, the mold 6 closes to accept the next shot of plasticized gelatin 14. All of these operations are automated and controlled by a microprocessor as hereinafter described.

Figure 3:
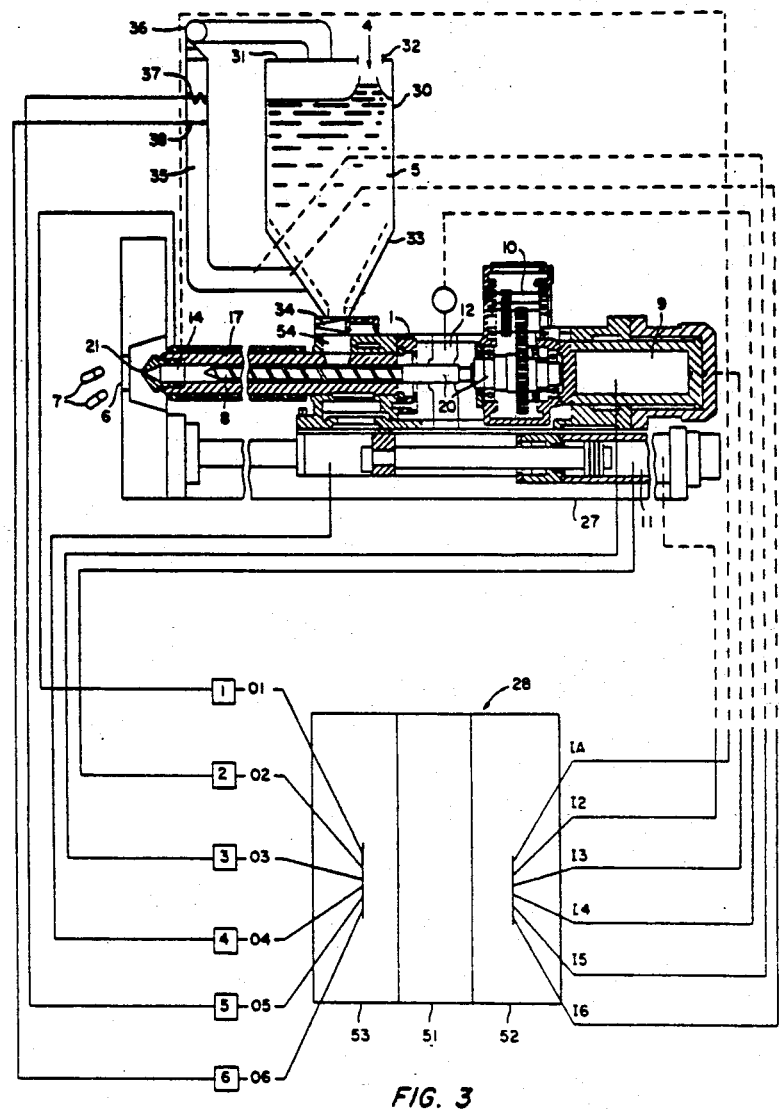
FIG. 3 is a schematic of the combined injection device-microprocessor apparatus for capsule parts.

Referring now to FIG. 2 and and also to FIG. 3. The injection molding work cycle of FIG. 2 is accomplished on the injection molding device 27 of FIG. 3 by hydraulic and electrical components and the corresponding circuits controlled by the microprocessor 28 of FIG. 3.

Through the use of solid-state circuitry and speed, temperature, limit and pressure switches for the electric and hydraulic systems, the microprocessor 28 of the present invention utilized command signals in its memory 51 for the parameters of time, temperature and pressure conditions of Table 1 below for the injection molding work cycle of FIG. 2 to be accomplished by the injection molding device 27 of FIG. 3 in producing gelatin capsule parts 7.

|  | POINTS | | | | |
| --- | --- | --- | --- | --- | --- |
|  | A | B | C | D | E |
| Time (seconds) | $10^{-2}$–1 | $10^{-2}$–1 | $10^{-2}$–1 | $10^{-2}$–1 | $10^{-2}$–1 |
| Temperature (°Celsius) | ambient–100 | 50–190 | 50–190 | 50–190 | 50–190 |
| Pressure ($10^5 \times N \times m^{-2}$) (Newtons per square meter) | 1–5 | 600–3000 | 600–3000 | 0–3000 | 600–3000 |

Referring now to FIG. 3 illustrating the combined injection molding device 27 and microprocessor 28 utilizing the method of present invention.

The combined injection molding device 27 and microprocessor 28 comprises six control circuits of which five are closed-loop, fully analog, and one is on-off. Starting at molding cycle Point A in FIG. 2, the injection molding work cycle operates as follows:

When sufficient plasticized gelatin 14 has accumulated in front of the screw 8 (microprocessor time controlled) and also when the screw assembly 20 carrying the screw 8, drive 10 and hydraulic motor 9 has been pushed far enough backwards against a constant backpressure as controlled by control circuit 3, limit switch 12 will be actuated by position sensing circuit 14. Upon these two conditions control circuit 4 is actuated causing the hydraulic fluid to flow into the forward portion of the hydraulic cylinder 11. This rams the screw assembly 20 forward, thus injecting the plasticized gelatin 14 into the mold 6 as molding cycle Point B of FIG. 2 is reached, and, as controlled by the microprocessor 28, the screw 8 remains stationary in this forward position under high pressure for a certain period of time until Point C.

From molding cycle Point B of FIG. 2 onwards the plasticized gelatin 14 cools down in the mold 6 and the port 21 closes at molding cycle Point C of FIG. 2.

At molding cycle Point C of FIG. 2 the screw 8 starts to rotate again and the hydraulic pressure reduced from the forward portion of the hydraulic cylinder 9 to a pressure slightly less than the pressure set for the backward portion of the hydraulic cylinder 9.

The barrel 17 is kept under constant pressure towards the mold 6 by the pressure in the back position of the hydraulic cylinder 11. This is achieved by means of the control circuit 2 where a proportional hydraulic valve is controlled by a pressure sensor circuit $I_2$.

As the screw 8 rotates a recharge of gelatin 4 is made from the hopper 5. During a certain time period and at a defined rotating speed of the screw 8, controlled by control circuit 3, a precise amount of gelatin 4 is fed into the extruder barrel 17. Control circuit 3 is actuated by speed sensor circuit $I_3$ measuring the rotating speed of the screw 8 and sensing back to a hydraulic proportional flow control valve $0_3$ controlled by control circuit 3, thus assuring a constant rotating speed of the hydraulic motor 10, irrespective of the changing torque resulting from introduction of the gelatin 4 recharge.

When the load time is completed, the screw 8 rotation is stopped and molding cycle Point D of FIG. 2 is reached. The soak time from molding cycle Points D to A of FIG. 2 allows for the gelatin 14 to plasticize completely under controlled temperature conditions as controlled by control circuit 1.

A temperature sensor circuit $I_1$ senses a thyristor heat regulator $0_1$ heating the extruder barrel 17 as directed by control circuit 1.

During the time interval from molding cycle Points B to E on FIG. 2, the mold 6 has cooled down sufficiently so that the finished capsule parts 7 can be ejected from the mold 6.

After ejection of the capsule parts 7, the work cycle returns to Point A of FIG. 2 where a certain volume of plasticized gelatin 14 has accumulated in front of the screw 8 (sensing circuit $I_4$ is actuated and time has elapsed) so that the work cycle of FIG. 2 can be repeated.

It is important to note the temperature and humidity control loops 5 and 6, for the maintenance of precise water content of the gelatin in the hopper 5, which is essential for proper operation at the desired speeds.

The microprocessor 28 includes a memory section 51 to store the desired operating parameters; a sensing and signaling section 52 to receive the sensing signals of actual operating conditions, to detect the deviation between the desired and actual operating conditions, and to send signals for adjustment through the actuating section 53 to the thyristors and valves.

Figure 4:
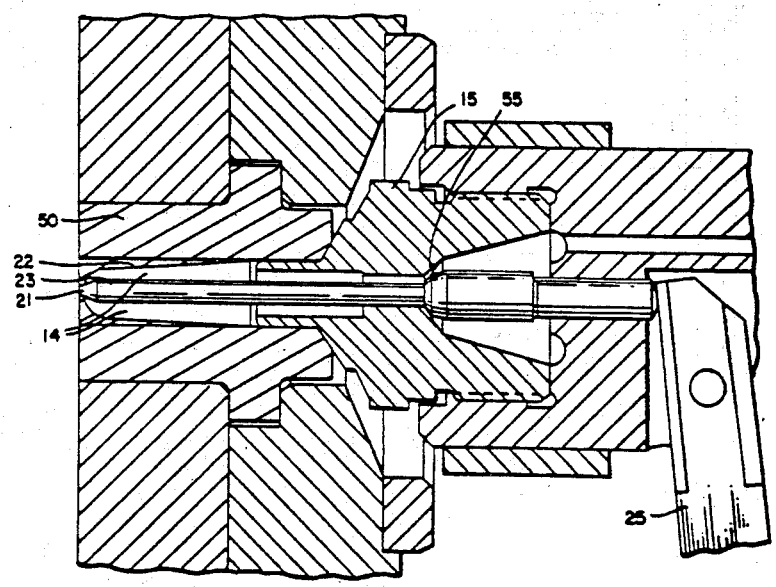
FIG. 4 is an expanded schematic of the exit end of the injection molding device.

Referring now to FIG. 4 there is shown the valve assembly 50 including the outlet port 21, the nozzle 22, the needle valve 23, and the one-way valve 15. These elements operate as follows:

At Point A in FIG. 2 the needle valve 23 is retracted from the outlet port 21 and the one-way valve 15 is retracted from the valve body 50 so as to form an inlet opening 55 for plasticized gelatin 14 into the nozzle 22 which defines a charging chamber for plasticized gelatin 14. The plasticized gelatin 14 is injected through nozzle 22 and into the mold 6 during the mold-filling time between Point A and B in FIG. 2. At Point C in FIG. 2 the needle valve 23 is pushed forward so as to close the outlet port 21 during which time between point C and E in FIG. 2, the mold 6 is closed and the capsule part 7 in the mold 6 is cooling. The needle valve 23 remains closed between Point E and A in FIG. 2 during which time the capsule part 7 is ejected from the mold 6. The total time period between Point B and A in FIG. 2 must be less than 5 seconds in order that the plasticized gelatin 14 does not solidify in the nozzle 22. This is an important aspect of the present invention because:

a. faster production times are made possible in order to achieve greater output;

b. there is no loss of plasticized gelatin 14 in the production cycle due to solidification in the nozzle 22 and the mold 6; and c. there is a minimum risk of degradation of the plasticized gelatin 14 because it remains in the production cycle for a short time and is only utilized once in each production cycle because the plasticized gelatin 14 is solidified in the capsule-shaped cavities 19 and not in the nozzle 22.

The one-way valve 15 and the needle valve 23 are actuated by a spring-tensioned lever 25 which normally closes both the outlet port 21 and the nozzle 22 until the lever 25 is cam-actuated pursuant to signals from the microprocessor 28.

The thermomechanical properties of gelatin, i.e. storage and loss shear modules at different temperatures, are strongly dependent on its water content. The capsule molding process of the present invention can be used for gelatin with a water content preferably within a range of 5 to 25%. The lower limit is defined by the maximum processing temperature of 190° C., which in turn cannot be exceeded in order to avoid degradation. The upper limit is determined by the stickiness of the finished capsules. The abbreviations in Table 2 below will be used hereinafter in this application:

TABLE 2

Abbreviations of Used Physical Parameters

| ABBREVIATION | UNIT | DESCRIPTION |
|---|---|---|
| Ta,Pa | Degree C., $N \times m^{-2}$ | Ambient temperature and pressure. |
| H(T,P) | $KJoule \times Kg^{-1}$ | Enthalpy of the hydrophilic polymer-water system at a given pressure and temperature. |
| $\delta$(T,P) | $N^{-1} \times m^2$ | Compressibility of the hydrophilic polymer at a given temperature and pressure. Its numerical value is the relative volume change due to change of pressure by a unit amount. |
| $\alpha$(T,P) | $(Degree\ C.)^{-1}$ | Volumetric thermal expansion coefficient of the hydrophilic polymer at a given temperature and pressure. Its numerical value is the relative volume change due to change of temperature by a unit amount. |
| V(g,T,P) | $Kg \times sec^{-1}$ | Flow rate of the hydrophilic polymer at a given temperature and shear deformation rate and pressure. Its |

TABLE 2-continued
Abbreviations of Used Physical Parameters

| ABBREVIATION | UNIT | DESCRIPTION |
|---|---|---|
| | | numerical value is the volume of a melt leaving the exit crosssectional area of an injection molding device in unit time due to the applied shear deformation rate. |
| $T_{G1}; T_{G2}(X)$ | Deg C. | The temperature range of the glass-transition of the hydrophilic polymer. |
| $T_{M1}; T_{M2}(X)$ | Deg C. | The temperature range of the melting of the partially crystalline hydrophilic polymer. |
| $T_E(t)$ | Deg C. | The temperature of the hydrophilic polymer in the nozzle area of the injection unit. |
| $T_M(t)$ | Deg C. | The temperature of the hydrophilic polymer in the mold. |
| $P_M$ | $N \times m^{-2}$ | The pressure of the hydrophilic polymer in the mold. |
| $P_E$ | $N \times m^{-2}$ | The pressure in the nozzle area of the hydrophilic polymer, expressed as the weight fraction of the water - hydrophilic polymer system. |

For the control and regulation of the injection molding process (IMP) we need the knowledge of the (1) heat consumption of the melting process:

$$H(T_E, P_E) - H(T_a, P_a)$$

(2) the heating rates of the hydrophilic polymers in the injection molding device. To calculate this we need the heat conduction number of the hydrophilic polymer and the heat transfer number of the hydrophilic polymer and the specific material of construction of the barrel which is in contact with the hydrophilic polymer. The heating rate and the heat consumption of the hydrophilic polymer give the minimum time interval necessary to make the hydrophilic polymer ready to inject and the necessary heating power of the injection molding device.

(3) the $T_E$ depends on X of the hydrophilic polymers. If the water content of the hydrophilic polymer in the mold is too low the resulting $T_E$ will be too high and cause degradation. A minimum water content of 5% by weight is required to keep $T_E$ below 190° C.

(4) the flow rate $V(g,T,P)$ is as well strongly dependent on the water content of the hydrophilic polymer. To speed up the IMP we need a high flow rate $V(g,T,P)$ which can be achieved by a higher water content.

The upper limit of the water content is defined by the stickiness and mechanical failure of the capsules; a water content of 25% (0.25) by weight cannot be generally exceeded. The range within which capsules can be molded by the method of the present invention is therefore within 0.05 to 0.25 of water content. Better capsules are made with a water content in the range between 0.10 and 0.20; the best capsules were made with the water content in the range between 0.12 and 0.18.

The hydrophilic polymer in the mold will reduce its volume due to the temperature change $T_M - T_a$. This would result in voids and diminution of size of the capsule, which therefore would be of unacceptable quality. It is an absolute requirement in capsule making that the dimensional deviations are less than 1%. To compensate for shrinking by the temperature change the mold must be filled at a distinct pressure $P_M$. This filling pressure is determined by the quantities $\alpha(T,P)$ and $\delta(T,P)$. The injection pressure $(P_E)$ depends again on $T_E$, which as was shown already is in turn strongly dependent on X.

Referring now to FIG. 5, the shear rate dependent shear viscosity of gelatin at 90° C. is shown for gelatin with a water content X of 0.17. The capillary has a diameter of $d=1.05$ mm, and a length of 5.0 mm; the ratio of length to diameter is therefore $L/d=4.75$.

Figure 6:
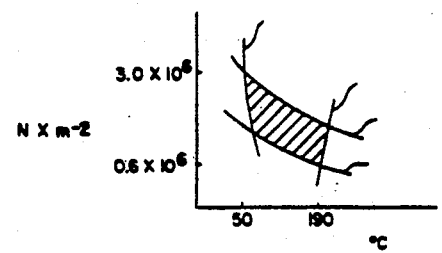
FIG. 6 is the diagram of molding area for gelatin within the ranges of time, temperature, pressure and water content of gelatin for the present invention.

Referring now to FIG. 6, the molding area diagram for gelatin with water content of 0.17. During injection molding the plasticized gelatin is discontinuously extruded and immediately cooled in a mold of the desired shape of the capsule part. Moldability depends on the gelatin properties and the process conditions, of which the thermomechanical properties of the gelatin as well as the geometry and the temperature and pressure conditions of the mold are the most important. In the molding area diagram of FIG. 6 the limits of pressure and temperature are indicated for the processing of gelatin in the combined injection molder-microprocessor of the present invention. The maximum temperature of 190° C. is determined by visible degradation of the gelatin above that limit. The lower temperature limit of 50° C. was determined by the development of too high viscosity and melt elasticity in the recommended water content range X: 0.05 to 0.25. The higher pressure limits of $3 \times 10^8 \, N \times m^{-2}$ are given by the start of flashing when the melted gelatin flows in a gap between the various metal dies which make up the molds, thus creating thin webs attached to the molded gelatin capsule parts at the separating lines. The lower pressure limits of about $6 \times 10^7 \, N \times m^{-2}$ are determined by short shots, when the mold cannot be completely filled by the gelatine.

WORKING PARAMETERS FOR INJECTION MOLDING PROCESS

| | |
|---|---|
| Density | $1.3–1.2 \times 10^3 \, kg \times m^{-3}$ |
| Crystallinity | 25% |
| $H(T_E,P_E)-H(T_a,P_a)$ | $0.32 \, KJoule \times kg^{-1}$ |
| Net heating performance for 10 kgs. melt/h (corresponding to $10^6$ capsules/h) | $3.5 \times 10^5 \, KJoule$ |
| Heat conduction number (20° C.) for gelatin | $1.0 \, KJoule \times m^{-1} \times h^{-1} \times Degree^{-1}$ |
| Compressibility $\delta(T_E,P_E)$ | $5 \times 10^{-10} \, N^{-1} \times m^2$ |
| $\alpha(T_a,P_a)$ | $8 \times 10^{-5} \, (Degree \, C.)^{-1}$ |
| Contraction due to crystallization | negligible |
| Critical shear deformation rate | $10^4–10^5 \, sec^{-1}$ |

Figure 7:
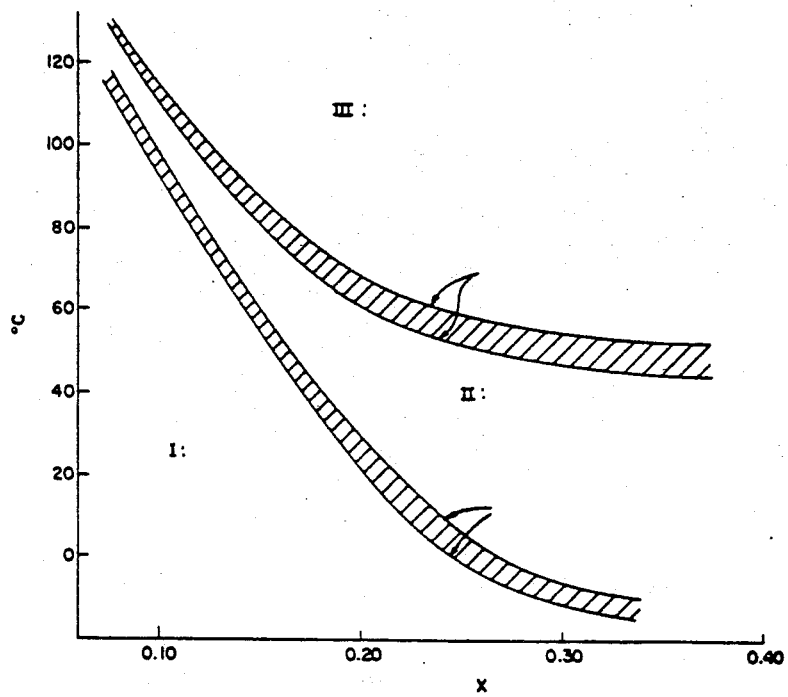
FIG. 7 is the diagram of dependence of glass transition temperature range and melting temperature range for the pertinent water content ranges of the gelatin.

The hydraulic polymers preferably various types of gelatin are extruded and injected under the following conditions:

Referring now to FIG. 7 the glass transition range and the melting temperature range as a function of the composition of the gelatin-water system is shown. At temperatures below the glass transition range ordinary gelatin, as available commercially, is a partially crystalline hydrophilic polymer containing approximately 70% amorphous and approximately 30% crystalline parts by volume (Area I in FIG. 7). Such gelatin preparations are commonly called cold dryed gelatins. By raising the temperature of said gelatin preparation at a distinct water content the gelatin passes through the glass transition range.

Figure 8:
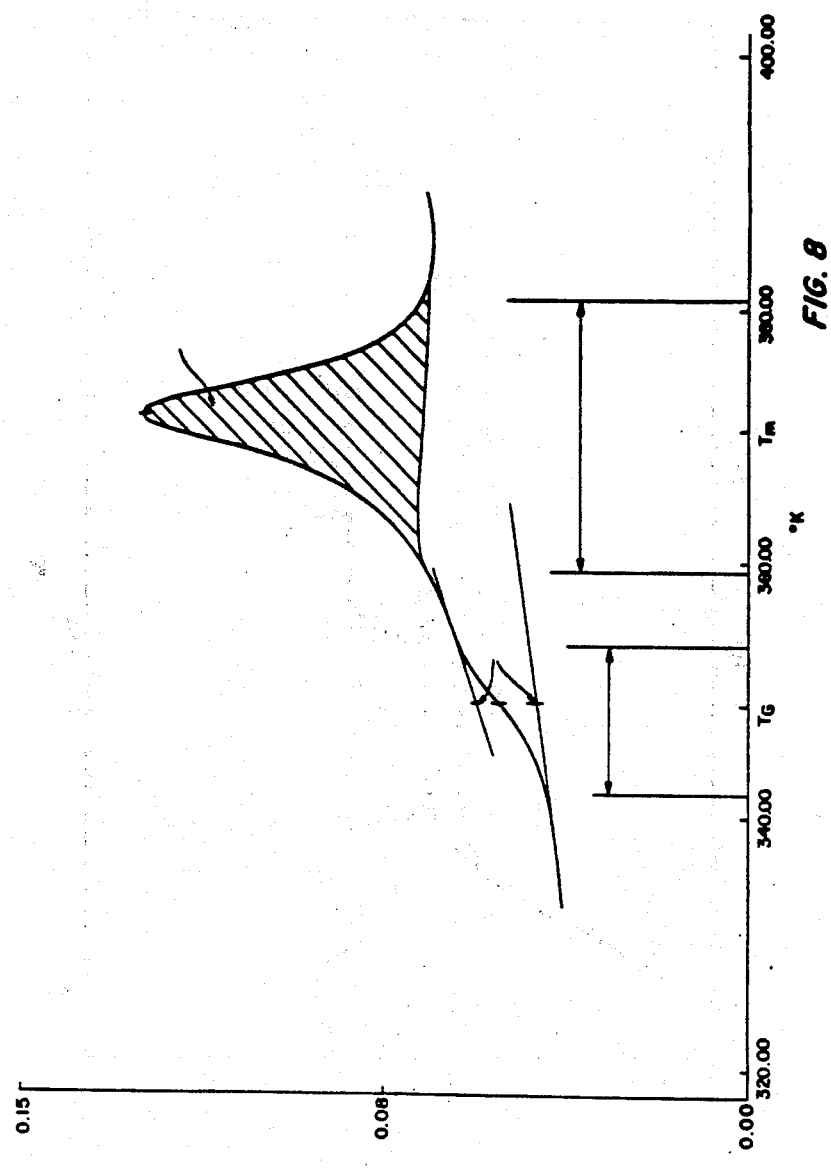
FIG. 8 is the diagram of dependence of differential calorimeter scan in which the heat consumption rate of the gelatin is plotted for the pertinent temperature range of the present invention.
Figure 9:
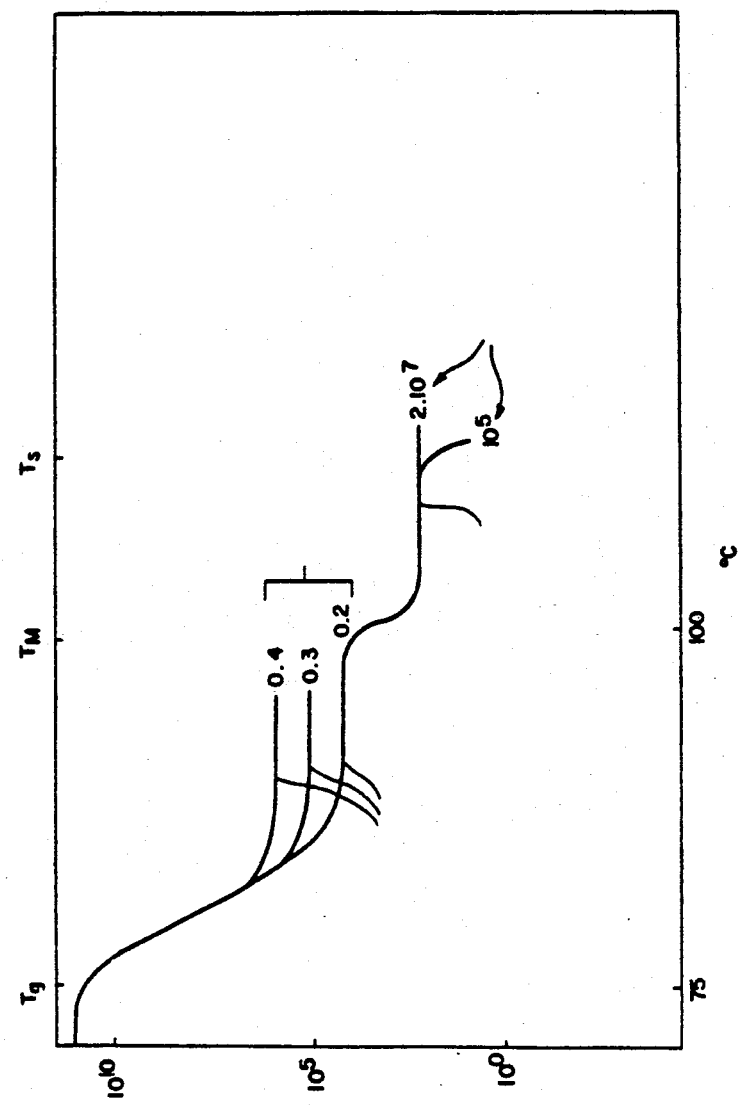
FIG. 9 is a diagram of dependence of the logarithmic bulk elastic storage module of the gelatin for the pertinent temperature range of the present invention.

Referring to FIG. 1 said heating process of the gelatin will take place within the extruder barrel 17. Referring to FIG. 2 said heating process of the gelatin will take place during the entire injection molding work cycle. The area in FIG. 7 between the glass transition range and the melting range is called Area II. In area II we find crystalline gelatin and a gelatin melt. The glass-transition is not a thermodynamic transition range of any order but is characterized by a change of the molecular movement of the gelatin molecules and by a change of the bulk storage module of the amorphous gelatin by several orders of magnitude. By passing from area II to area I in FIG. 7 the translational movements of the gelatin molecules or those of large parts of said molecules will be frozen in the glass transition temperature range and this is reflected by a change in the specific heat ($c_p$) and the volumetric thermal expansion coefficient (a) in said temperature range. By passing from area II to area III due to crossing the melting range of the crystalline gelatin the helically ordered part of the gelatin will melt. Referring to FIG. 1 said heating process of the gelatin will take place within the extruder barrel 17. Referring to FIG. 2 said heating process of the gelatin will take place during the entire injection molding work cycle. Said helix-coil transition is a true thermodynamic transition of the first order and is an endothermic process. Said transitions can be detected by scanning calorimetry or by measurement of the change of the linear viscoelastic bulk storage module due to change of the temperature. A typical plot of a temperature scan with a differential calorimeter is shown in FIG. 8. On the ordinate is plotted the velocity of the heat consumed by the sample relative to a reference (empty sample holder). The velocity of heat consumption of the sample is due to the change of the temperature of the gelatin sample, and said temperature is plotted on the abscissa as degrees of kelvin. The base line shift on said plot is corresponding to the glass transition and the peak to the melting or to the helix-coil transition. The linear viscoelastic bulk storage module E can be measured at small sinusoidal shear deformations of the gelatin sample. The changes of said module of a typical gelatin sample at water content X=0.13 is plotted as a function of the sample temperature in FIG. 9. At the glass transition temperature and at the melting or helix-coil transition temperature said module changes several orders of magnitude. As is shown in FIG. 9 there exist a further transition temperature above the melting range, and said transition is characterized by a further drop in said module E. We will call the temperature of said transition the solution temperature. In the temperature range $T_g$ to $T_M$ the gelatin is in the rubber elastic state, and the crystalline ranges or fibrills represent the elastically active elements of the network.

Similar networks exist in the plasticized microcrystalline polyvinylchloride (PVC). The crystalline regions give rise to diffraction patterns of x-rays in said PVC but not in the gelatin [I. Tomka, Chimia 30, 534–540 (1976); I. Tomka et al. Phot. Sci. 23, 97 (1975)]. In the temperature range $T_M$ to $T_S$ the gelatin is in the viscoelastic rubber-elastic state. The elastically active network in said state of the gelatin is like in most polymer melts a temporary network. Said temporary network is due to entanglements of the polymer molecules. Specifically in the gelatin the strong interactions between the macromolecules (hydrogen-bridges, dipol-dipol interactions) contribute an important part to the elastically active temporary network. At the solution temperature said temporary network disrupts and the gelatin molecules specifically due to the presence of water dissolve. At a temperature higher than $T_S$ the storage module drops to extremely low values: less than $10 \times Nm^{-2}$, as shown in FIG. 9. In the present invention it was found that the processing (injection molding, blow molding etc.) of the gelatin should proceed at a temperature higher than $T_S$.

Referring to FIG. 1 the heating of the gelatin to a temperature higher than $T_S$ takes place in the forward part of the extruder barrel 17. Said heating process will be maintained not only by the steam heating coils 18 but to an important proportion by the internal friction during the injection process due to the high deformational rates. Referring to FIG. 2 said dissolution process will take place especially between point A and B of the work cycle. It was found that the reversible elastic deformation of the injection molded gelatin after opening the mold 6 is negligible if the temperature of the gelatin during the injection process is higher than $T_S$, otherwise the molding sequence would drop by at least an order of magnitude.

Referring to FIG. 2 the necessary cooling period for the gelatin in the molds—to prevent any reversible elastic deformation of said gelatin—will take place between points B and E of the working cycle. A restriction of the molding sequence to low speed coupled with long keeping of the gelatin in the mold (larger than 5 sec) is undesirable because of two reasons: low output of the product and loss of water content of the gelatin in the extruder. At the elevated injection temperature there is always a transport of water from the hot to the cold gelatin in the extruder barrel. (See D. Gehrmann, Thesis, University of Darmstadt 1979). Said water transport can be compensated due to the transport of the gelatin by the screw in the opposite direction.

Figure 11:
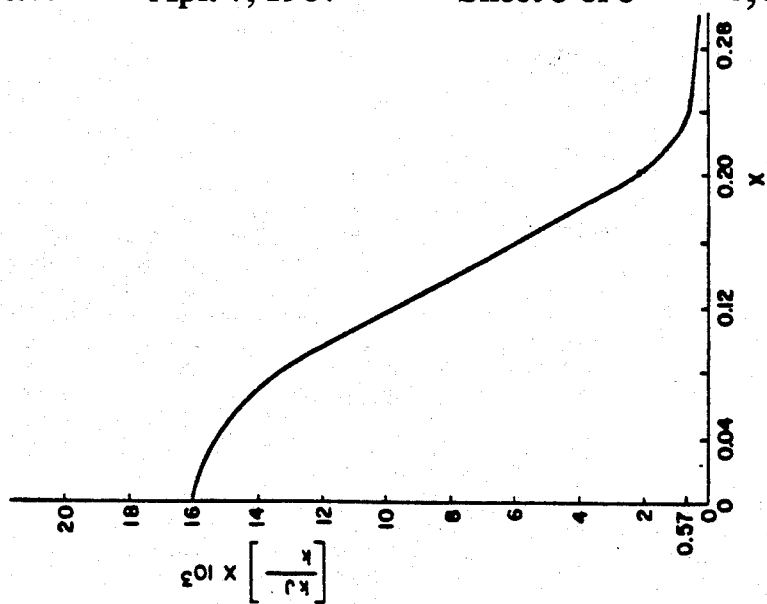
FIG. 11 is a diagram of dependence of differential heat of water adsorption in the pertinent range of water content of the gelatin of the present invention.
Figure 10:
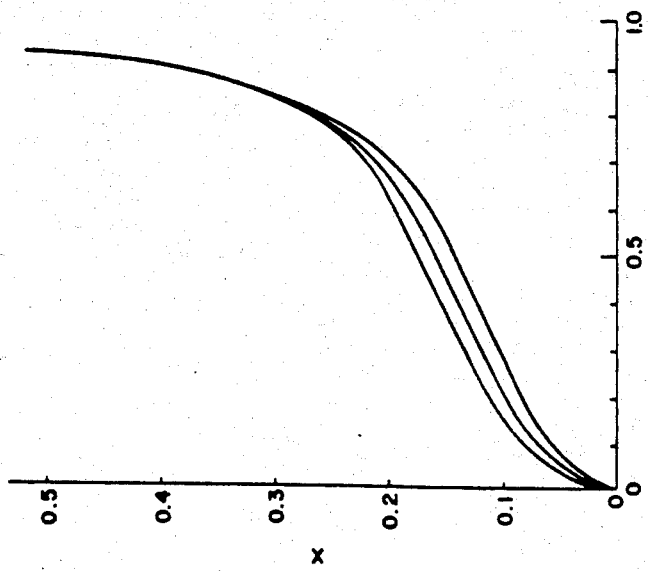
FIG. 10 is a diagram of dependence of equilibrium water content of the gelatin in the entire water activity range.

Referring to FIG. 1 said transport of gelatin will be maintained by screw 8. Referring to FIG. 2 said transport of gelatin will take place between the points A and B and further between the points C and D of the working cycle. To build up a stationary water content of the gelatin in the melting area of the extruder barrel it is necessary to work at an injection sequence which is shorter than 5 sec. To establish a constant and high enough water content of the gelatin in the extruder barrel it is further necessary to use gelatin or other hydrophilic polymers with the proper shape of both the sorption isotherm (see FIG. 10) and differential heat of sorption as a function of the water content (see FIG. 11). The constant water content of the gelatin in the extruder barel is necessary due to the maintenance of constant production conditions. The water content of the gelatin during the injection must fulfill the condition: X higher than 0.05 otherwise $T_S$ is also higher than 190° C. and this is undesirable due to degradation of the gelatin. The sorption isotherm of the gelatin shows an S-shape with an inflection point at about 0.5 water activity monotonously and the differential heat of sorption is a decreasing function with the water content. The condition which is necessary to avoid is a phase separation of the gelatin-water phase into the two liquid phases of gelatin-water and water. This phase separation could result in the extruder barrel during injection and is avoided by having water activity ($a_{W,M}$) of the gelatin (at the highest temperature in the extruder barrel and for the water content range of 0.05 to 0.25 of the gelatin) less than one.

By the present invention we could drop the processing temperature of a hydrophilic polymer by at least 100° C. which means we could shift the processing temperature ($T_p$) by incorporating sufficient water (X is more than 0.05 and less than 0.25) during processing of said hydrophilic polymer leading to a range of the temperature 50° to 190° C. where no degradation of said hydrophilic polymer during the processing takes place. The melting range of a typical gelatin with water content X is less than 0.002 (which water content is common during the processing of polyamides which are in their chemical structure similar to the gelatin) is between 220° and 250° C. This melting range is again comparable with the melting range of aliphatic polyamides. Polyamides for example show a different behaviour with respect to their compatibility with water during processing. The sorption isotherm of nylon 6 for example has no inflection point, its differential heat of sorption is not a monotonously decreasing function with the water content and already at room temperature the sorption isotherm shows an equilibrium water activity value equal to a water content for 0.05. If we now incorporate about 0.035 water content in said polyamide at ambient temperature we will find already a phase separation of water and water-polyamide phases below 100° C. Because the nylon 6 polymer is not molten at the said water content and at temperatures below 100° C. said polyamide is not processable. At a water content of 0.035 and temperatures equal to or higher than 100° C. the said polyamide is again not processable due to the syneresis of water in the extruder and the mold. This effect is well known in the corresponding literature (Kunstsoff Handbuch, Volume 6: Polyamide, Editors: R. Viewegen, A. Muller, Karl Hanser Verlag, Munich, W. Germany 1966).

In the procedure of branching and crosslinking of hydrophilic polymers, preferably various types of gelatin, it is important to add the crosslinking agents, especially the covalent crosslinking agents, shortly before injection of the molten hydrophilic polymers.

Referring now to FIG. 9 of the present invention it can be concluded that an increase of the molecular weight of said hydrophilic polymers would raise the solution temperature of said polymers.

Due to possible degradation at elevated processing temperature it is not desirable to branch or crosslink said hydrophilic polymers before injection.

Referring to FIG. 1, an aqueous solution of crosslinking agents is injected in front of a mixing system being placed between the melting and plasticizing unit 4 and the injection unit 1. The crosslinking reaction mainly occurs during the injection cycle and the time after ejection of the capsule. By the above described technology on branching and crosslinking there is no disadvantage of changing the thermomechanical properties of the hydrophilic polymers during the melting and solution process.

The hydrophilic polymers preferably various types of gelatin are extruded and injected under the following conditions given in Table 3 below:

TABLE 3

| Injection Conditions for Hydrophilic Polymers | | | |
|---|---|---|---|
| Injection Unit | | | |
| Screw diameter mm | 24 | 28 | 32 |
| Injection pressure N $\times$ m$^{-2}$ | $2.2 \times 10^8$ | $1.6 \times 10^8$ | $1.2 \times 10^8$ |
| Calculated swept volume cm$^3$ | 38 | 51.7 | 67.5 |
| Effective screw length L:D | 18.8 | 16.1 | 13.5 |
| Plasticising capacity (PS) kg/h(max.) | | | |
| 1a) | 13.5 | 21.2 | 21.5 |
| 11a) | 9.2 | 14.5 | 15 |
| 1b) | 23.6 | 34 | 36 |
| 11b) | 17.5 | 27 | 27.5 |
| Screw stroke mm (max.) | 84 | 84 | 84 |
| Injection capacity kW | 30 | 30 | 30 |
| Injection velocity mm/s(max.) | 460 | 460 | 460 |
| Nozzle contact force kN | 41.2 | 41.2 | 41.2 |
| Screw rotating speed min$^{-1}$ | | | |
| Var. 1a) | | 20 | - 280 |
| 11a) | | 20 | - 170 |
| Var. 1b) | | 20 | - 600 |
| 11b) | | 20 | - 400 |
| Number of heading zones | 5 | 5 | 5 |
| Installed heating capacity kW | 6.1 | 6.1 | 6.1 |
| Molding unit | | | |
| Clamping force kN | | | 600 |
| Opening stroke mm | | 100 | - 250 |

In addition to the present invention for molding capsules, one skilled in the art could also use this disclosure to produce capsules utilizing profile extrusion, compression molding, vacuum forming, thermal forming, extrusion molding polymer casting in combination with vacuum forming.

While the preferred embodiment of the injection molding-microprocessor apparatus is for the method of producing gelatin capsules from various gelatin types, it has been found that quality capsules may also be manufactured utilizing the present invention with gelatin preferably of lower quality modified just before injection by covalent and/or non-covalent crosslinking agents such as: multivalent metal salts such as aluminum and calcium salts, boric acid, potassium alum, ammonium alum and the like; metal salts of chromium, aluminum or zirconium (chromium acetate, chromium alum) as described in patent Nos. DT 24 39 553 A1, DT 26 26 026 A1, DT 21 48 428, and DT 25 05 746; aldehydes and ketones as well as their halogenated derivatives as formaldehyde, paraformaldehyde, 2, 4, 6, trinitro-benzaldehyde, quinones (benzoquinone), 1,2 and 1,3 dicarbonyl compounds such as glyoxal, cyclohexandion-1,2; 1,5 dialdehydes (glutaraldehyde); acids and acid anhydrides such as mucochloric acid, chlorides of 2-basic organic acids, anhydrides of tetracarboxylic acids; compounds with more than 2 easy-breaking hetrocyclic 3-membered rings as ethylene oxide and ethylenimine; polyfunctional methene-sulfonic acid esters; non nitrogen polyfunctional compounds including ethylene glycoldimethacrylate, diepoxy butane, epichlorohydrin, dichloropropanol, diethylene glycoldimethacrylate, dichloromethyl and dichlorooctyl ethers and the like; nitrogen containing polyfunctional compounds as e.g. hexamethylene diisocyanate, dimethyl adipimate, bisdiazobenzidine, Woodward's reagent K, N,N'-(1,3-phenylene) bismaleimide, N,N'-ethylene-bis-(iodoacetamide), urea, trichloro isocyanuric acid, ethylene-bismethacrylamide, tetrachloropyrimidine, dimethylol urea, dimethylol ethylene urea, methylol and dimethylol acrylamide as well as the following group of crosslinking agents described in the patent Nos. De 23 48 294 B2, DT 24 39 553 A1, DT 25 05 746 A1, DT 26 25 026 A1, EUR 0,021,108, U.S. Pat. No. 3,321,313, and DT 21 48 428;
carbodiimides;
sulfobetain carbodiimides;
carbamoyl oxypyridinium salts;
carbamoylonium salts;
1-N-ethoxy-carboxy-2-ethoxy-dihydrochinoline;
isoxazolium salts;
bis-isoxazolium salts; and
diisocyanates.

For the manufacturing of capsules with the above described hydrophilic polymers the utilization of plasticizers, lubricants and coloring agents specifically of pharmaceutical grades leads to optimal product qualities.

Pharmacologically acceptable plasticizers, such as polyethylene glycol or preferably low-molecular weight organic plasticizers, like glycerol, sorbitol, dioctyl-sodium sulfosuccinate, triethyl citrate, tributyl citrate, 1,2 propylenglycol mono-, di-, tri-acetates of glycerol etc. are utilized at various concentrations of about 0.5-40% preferably at 0.5-10% based upon the weight of the hydrophilic polymer.

Pharmacologically acceptable lubricants, such as the stearates of aluminum, calcium, magnesium and tin; as well as talc, silicones, etc. are to be used at concentrations of about 0.1-10% preferably at 0.1-5% based upon the weight of the hydrophilic polymer.

Pharmaceutically acceptable coloring agents, such as azo-dyes and other dyestuffs and pigments as iron oxides, titanium dioxides, natural dyes etc. are used at concentrations of about 0.001-10% preferably at 0.001-5% based upon the weight of the hydrophilic polymer.

In addition it has been found that the injection molding-microprocessor apparatus of the present invention can produce quality capsules with various grades of gelatin combined with extenders in amounts up to as much as 95% content, by weight, in some instances such as sunflower proteins, soybean proteins, cotton seed proteins, peanut proteins, rape seed proteins, lactose, gum arabic (a polysaccharide of partially substituted 1,3-D-galactopyranose units), acrylates and methacrylates (eudragit), cellulose and water soluble derivatives of cellulose like cellulose acetyl phthalate (CAP), hydroxyetaye cellulose, methyl cellulose, sodium carboxymethyl cellulose, hydroxypropyl methylcellulose, hydroxypropyl methylcellulosephthalate (HPMCP), hydroxymethylcellulose, acrylic acid polymers polyvinylpyrrolidone, shellac, bentonite, polyvinyl-acetatephthalate, phthalated geletin, succinated gelatin, crotonic acid; and polysaccharides like agar-agar (an alternating co-polymer $\beta$-D-galactopyranosyl and 3,6-anhydro-$\alpha$-L-galactopyranosyl residue linked in the 1,3 position).

For the manufacturing of capsules with the above described polymers the utilization of plasticizers, lubricants and coloring agents preferably of pharmaceutical grades leads to optimal product qualities.

Pharmacologically acceptable plasticizers, such as polyethylene glycol or preferably low-molecular weight organic plasticizers, like glycerol, sorbitol, dioctylsodium sulfosuccinate, triethyl citrate, tributyl citrate, 1,2 propylenglycol, mono-, di-, tri-acetates of glycerol etc. are utilized at various concentrations of about 0.5-40% preferably at 0.5-10% based upon the weight of the hydrophilic polymer.

Pharmacologically acceptable lubricants, such as the stearates of calcium, magnesium, tin, as well as talc, silicones, etc. are to be used at concentrations of about 0.1-10% preferably at 0.1-5% based upon the weight of the hydrophilic polymer.

Pharmacologically acceptable coloring agents, such as azo-dyes and other dyestuffs and pigments as iron oxides, titanium dioxides, natural dyes etc. are used at concentrations of about 0.001-10% preferably at 0.001-5% based upon the weight of the hydrophilic polymer.

In addition it has been found that quality capsules can be made with the injection molding-microprocessor apparatus utilizing the method of the present invention with other polymers having enteric properties (2 hours resistant in gastric juice, soluble within good 30 min in intestinal juice according to USP XX) as: hydroxypropyl methylcellulosephthalate (HPMCP), polyvinylacetatephthalate (PVAP), celluloseacetylphthalate (CAP), acrylates and methacrylates (eudragit), phthalated gelatin, succinated gelatin, crotonic acid, and shellac. Said polymers having enteric properties may be combined with various extenders such as various grades of gelatin and/or gelatin modified by covalent and non-covalent crosslinking agents or combinations of more than one covalent and non-covalent crosslinking agents, vegetable proteins as sunflower proteins, soybean proteins, cotton seed proteins, peanut proteins, rape seed proteins, blood proteins, egg proteins, and acetylated derivatives thereof and the like, alginates (linear multiblock copolymers of blocks of $\beta$-(1,4)-D-mannuronic acid and $\alpha$-(1,4)-L-gluronic acid as well as alternating copolymers of both these principal constituents), lactose, gum arabic, cellulose and water soluble derivatives of cellulose such as hydroxyethylcellulose, hydroxypropylcellulose, hydroxypropylmethylcellulose, hydroxymethylcellulose, water soluble acrylic acid polymers, vinyl acetate polymers, agar-agar.

For the manufacturing of capsules with the above described polymers the utilization of plasticizers, lubricants and coloring agents specifically of pharmaceutical grades leads to optimal product qualities.

Pharmacologically acceptable plasticizers, such as polyethylene glycol or preferably low-molecular weight organic plasticizers, like glycerol, sorbitol, dioctyl-sodium sulfosuccinate, triethyl citrate, tributyl citrate, 1,2 propylenglycol, mono-, di-, tri-acetates of glycerol etc. are utilized at various concentrations of about 0.5-40% preferably at 0.5-10% based upon the weight of the hydrophilic polymer.

Pharmacologically acceptable lubricants, such as the stearates of aluminum, calcium, magnesium, tin, as well as talc, silicones, etc. are used at concentration of about 0.1-10% preferably at 0.1-5% based upon the weight of the hydrophilic polymer.

Pharmaceutically acceptable coloring agents, such as azo-dyes and other dyestuffs and pigments as iron oxides, titanium dioxides, natural dyes etc. are used at concentrations of about 0.001-10% preferably at 0.001-5% based upon the weight of the hydrophilic polymer.

In addition it has been found that quality capsules can be made with the injection molding-microprocessor apparatus utilizing the method of the present invention with other polymers as gelatin substitutes such as: vegetable proteins, as sunflower proteins, soybean proteins, cotton seed proteins, peanut proteins, rape seed proteins, blood proteins, egg proteins, and acetylated derivatives thereof and the like, gum arabic, water soluble derivatives of cellulose like hydroxyethylcellulose, hydroxypropylcellulose, hydroxypropylmethylcellulose, other water soluble carbohydrates like agar-agar, other water soluble polymers like acrylic acid polymers, polyvinylpyrrolidone and the like, and vinylacetate polymers.

For the manufacturing of capsules with the above described polymers the utilization of plasticizers, lubricants and coloring agents preferably of pharmaceutical grades leads to optimal product qualities.

Pharmacologically acceptable plasticizers, such as polyethylene glycol or preferably low-molecular weight organic plasticizers, like glycerol, sorbitol, dioctyl-sodium sulfosuccinate, triethyl citrate, tributyl citrate, 1,2 propylenglycol, mono-, di-, tri-acetates of glycerol etc. are utilized at various concentrations of about 0.5–40% preferably at 0.5–10% based upon the weight of the hydrophilic polymer.

Pharmacologically acceptable lubricants, such as the stearates of aluminum, calcium, magnesium and tin, as well as talc, silicones, etc. are to be used at concentrations of about 0.1–10% preferably at 0.1–5% based upon the weight of the hydrophilic polymer.

Pharmaceutically acceptable coloring agents, such as azo-dyes and other dyestuffs and pigments as iron oxides, titanium dioxides, natural dyes etc. are used at concentrations of about 0.001–10% preferably at 0.001–5% based upon the weight of the hydrophilic polymer.

EXAMPLES

1. Series with bone gelatin No. 1 at various water contents

To test the method and apparatus as described before according to the present invention, batches of gelatin with different water contents were prepared and conditioned and then tested in an injection molding machine at different working conditions. The bone gelatin No. 1 had the following molecular mass mean values:

| | | |
|---|---|---|
| Number (average): | 57000 | Dalton |
| Viscosity (average): | 155000 | Dalton |
| Weight (average): | 258000 | Dalton |
| Centrifuge (average): | 5130000 | Dalton |
| molecular mass of largest molecules: | $10^7$ | Dalton |

A batch of said gelatin in granulated form, with a mean diameter of the granules of 2 mm was conditioned as follows: The gelatin, whose original water content was 0.105 was filled into a drum and sprayed with a fine spray of water to the calculated water content as desired for each experiment. The 1% by weight of calcium stearate was added as a lubricant. The batch was then thoroughly mixed and stored in the closed drum for three days at ambient temperature. Several different series of experiment were made, each with a batch of gelatin with different water content. The temperatures at different points in the molding characteristics and quality of the capsules are given.

Referring to FIG. 2 the cycle times of the injection molding-microprocessor apparatus are as follows:

| Cycle Points | Times |
|---|---|
| A–B | variable, depending on temperature, see table 3 |
| B–C (soak time) | 1 minute |
| C–D (filling time) | 1 sec |
| D–E | 5 sec |
| E–A | 1 sec |

Pressure in the nozzle: $1.94 \times 10^6 \text{N} \times \text{m}^{-2}$

Temperatures at different points of screw: variable, see Tables 4–12 below

Temperature at the nozzle: variable, See Tables 4–12 below

In Table 4 below and the following tables for series A to I the abbreviation mean:

X: water content of gelatin $T_M$: melting temperature of the gelatin determined by differential scanning calorimetry $T_b$: temperature at beginning of screw $T_m$: temperature at middle of screw $T_e$: temperature at end of screw $T_g$: temperature at nozzle LFV: Linear flow velocity L: flow length D: film thickness

EXAMPLE 1

Acceptable gelatin capsules containing 1% by weight of calcium stearate were prepared and processed according to the working conditions tabulated in Table 4 below: Sample parameter: $T_M=92.8°$ C.; X=0.136

TABLE 4

| | $T_b$ | $T_m$ | $T_e$ | $T_g$ | L/D | LFV |
|---|---|---|---|---|---|---|
| A-1 | 105 | 110 | 110 | 100 | 114.3 | 72.4 |
| A-2 | 125 | 130 | 130 | 100 | 142.9 | 44.1 |
| A-3 | 135 | 150 | 150 | 100 | 171.4 | 40.0 |
| A-4 | 145 | 170 | 170 | 100 | 164.3 | 80.0 |

EXAMPLE 2

Acceptable gelatin capsules containing 1% by weight of calcium stearate were prepared and processed according to the working conditions tabulated in Table 5 below: Sample parameters: $T_M=86.8°$ C.; X=0.146

TABLE 5

| | $T_b$ | $T_m$ | $T_e$ | $T_g$ | L/D | LFV |
|---|---|---|---|---|---|---|
| B-1 | 105 | 110 | 100 | 100 | 45.7 | 75.0 |
| B-2 | 125 | 130 | 130 | 100 | 135.7 | 28.2 |
| B-3 | 135 | 150 | 150 | 100 | 157.1 | 61.3 |
| B-4 | 145 | 170 | 170 | 100 | 92.8 | 88.9 |

EXAMPLE 3

Acceptable gelatin capsules containing 1% by weight of calcium stearate were prepared and processed according to the working conditions tabulated in Table 6 below; Sample parameter: $T_M=85.8°$ C.; X=0.66

TABLE 6

| | $T_b$ | $T_m$ | $T_e$ | $T_g$ | L/D | LFV |
|---|---|---|---|---|---|---|
| C-1 | 105 | 110 | 110 | 100 | 92.9 | 66.7 |
| C-2 | 125 | 130 | 130 | 100 | 171.4 | 45.2 |
| C-3 | 135 | 150 | 150 | 100 | 157.1 | 24.7 |
| C-4 | 145 | 170 | 170 | 100 | 168.5 | 60.0 |

EXAMPLE 4

Acceptable gelatine capsules containing 1% by weight of calcium stearate were prepared and processed according to the working conditions tabulated in Table 7 below: Sample parameter: $T_M = 80°$ C.; $X = 0.174$

TABLE 7

|     | $T_b$ | $T_m$ | $T_e$ | $T_g$ | L/D | LFV |
|-----|-------|-------|-------|-------|------|------|
| D-1 | 95    | 85    | 85    | 100   | 64.3 | 25.0 |
| D-2 | 100   | 90    | 90    | 100   | 78.6 | 26.3 |
| D-3 | 105   | 95    | 95    | 100   | 92.9 | 30.3 |

EXAMPLE 5

Acceptable gelatin capsules containing 1% by weight of calcium stearate were prepared and processed according to the working conditions tabulated in Table 8 below: Sample parameter: $T_M = 75°$ C.; $X = 0.193$

TABLE 8

|     | $T_b$ | $T_m$ | $T_e$ | $T_g$ | L/D   | LFV  |
|-----|-------|-------|-------|-------|-------|------|
| E-1 | 75    | 90    | 95    | 100   | 85.7  | 55.6 |
| E-2 | 85    | 95    | 100   | 100   | 100.0 | 71.4 |
| E-3 | 100   | 100   | 110   | 100   | 142.9 | 41.7 |
| E-4 | 100   | 130   | 120   | 100   | 135.7 | 60.7 |
| E-5 | 130   | 150   | 130   | 100   | 157.1 | 51.9 |
| E-6 | 145   | 170   | 170   | 100   | 159.2 | 66.7 |

EXAMPLE 6

Acceptable gelatin capsules containing 1% by weight of calcium stearate were prepared and processed according to the working conditions tabulated in Table 9 below: Sample parameter: $T_M = 70°$ C.; $X = 0.208$

TABLE 9

|     | $T_b$ | $T_m$ | $T_e$ | $T_g$ | L/D   | LFV  |
|-----|-------|-------|-------|-------|-------|------|
| F-1 | 70    | 85    | 90    | 95    | 57.1  | 35.6 |
| F-2 | 75    | 90    | 95    | 100   | 52.9  | 30.8 |
| F-3 | 85    | 95    | 100   | 105   | 64.3  | 29.6 |
| F-4 | 100   | 100   | 110   | 110   | 100.0 | 25.8 |
| F-5 | 100   | 140   | 120   | 100   | 114.3 | 27.1 |

EXAMPLE 7

Bone gelatin No. 1 including the addition of a plasticizer

A batch of gelatin with a certain content of water and a plasticizer was prepared and conditioned and then tested in an injection molding device at different working conditions. A batch of bone gelatine No. 1 in granulated form with a mean diameter of the granules was conditioned as follows: The gelatin, whose water content was 10.54% was filled into a drum and sprayed with a specially fine spray of a mixture consisting of water and glycerol as plasticizer to the calculated content as desired. The 1% by weight of calcium stearate was added as a lubricant. The following procedure exactly corresponds to the measures taken for example series 1.

Acceptable gelatin was processed according to the working conditions tabulated in Table 10 below. Sample parameters: $T_M = 92°$ C. $X = 0.152$ Glycol content 3.5% by weight.

TABLE 10

|     | $T_b$ | $T_m$ | $T_e$ | $T_g$ | L/D   | LFV  |
|-----|-------|-------|-------|-------|-------|------|
| G-1 | 105   | 110   | 110   | 100   | 151.4 | 50.0 |
| G-2 | 125   | 130   | 130   | 100   | 171.4 | 40.0 |
| G-3 | 135   | 150   | 150   | 100   | 178.5 | 53.8 |

TABLE 10-continued

|     | $T_b$ | $T_m$ | $T_e$ | $T_g$ | L/D   | LFV  |
|-----|-------|-------|-------|-------|-------|------|
| G-4 | 145   | 170   | 170   | 100   | 170.0 | 57.1 |

Series with pigskin gelatin No. 2 at various water contents (Examples 8 and 9 below)

Pigskin gelatin No. 2 having the following molecular mass mean values was used:

| Number (average):                   | 34000 Dalton        |
|-------------------------------------|---------------------|
| Viscosity (average):                | 65000 Dalton        |
| Weight (average):                   | 80000 Dalton        |
| Centrifuge (average):               | 1450000 Dalton      |
| molecular mass of largest molecules: | $2 \times 10^6$ Dalton |

EXAMPLE 8

Acceptable gelatin capsules containing 1% by weight of calcium stearate were prepared and processed according to the working conditions tabulated in Table 11 below: Sample parameters $T_M = 80°$ C.; $X = 0.167$

TABLE 11

|     | $T_b$ | $T_m$ | $T_e$ | $T_g$ | L/D   | LFV  |
|-----|-------|-------|-------|-------|-------|------|
| H-1 | 105   | 110   | 110   | 100   | 164.3 | 52.9 |

EXAMPLE 9

Acceptable gelatin capsules containing 1% by weight of calcium stearate were prepared and processed according to the working conditions tabulated in Table 12 below: Sample parameters $T_M = 70°$ C.; $X = 0.202$

TABLE 12

|     | $T_b$ | $T_m$ | $T_e$ | $T_g$ | L/D   | LFV  |
|-----|-------|-------|-------|-------|-------|------|
| I-1 | 80    | 90    | 90    | 100   | 117.1 | 59.1 |
| I 2 | 105   | 110   | 110   | 100   | 135.7 | 90.0 |

EXAMPLE 10

Bone gelatin 80 bloom, grade A

A batch of gelatin with a certain content of water was prepared and conditioned and then tested in an injection molding machine. A batch of bone gelatin 80 bloom, grade A, in granulated form was conditioned as follows: The gelatin of which the water content was 13% was filled into a drum and sprayed with a specially fine spray of water to the calculated content as wanted. The batch was then throughly mixed and stored in the closed drum for half a day at ambient temperature. Acceptable gelatin capsules were then produced according to the working conditions listed on table 13 below: Material Composition: gelatin 80A: 85.3%; water: 14.7%

TABLE 13

| $T_b$ | $T_m$ | $T_e$ | $T_g$ | L/D | LFV |
|-------|-------|-------|-------|-----|-----|
| 110   | 125   | 135   | 135   | 66  | 840 |

EXAMPLE 11

Bone gelatin 150 bloom, grade A

A batch of gelatin with a certain content of water was prepared and conditioned and then tested in an injection molding machine. A batch of bone gelatin 150 bloom, grade A, in granulated form was conditioned as follows: The gelatin of which the water content was 12% was filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 14 below: Material Composition: gelatin 150A: 84.5%; water: 15.5%

TABLE 14

| $T_b$ | $T_m$ | $T_e$ | $T_g$ | L/D | LFV |
|---|---|---|---|---|---|
| 110 | 120 | 140 | 140 | 66 | 820 |

EXAMPLE 12

Bone gelatin 150 bloom, grade A

A batch of gelatin with a certain content of water was prepared and conditioned and then tested in an injection molding machine. A batch of bone gelatin 150 bloom, grade A, in granulated form was conditioned as follows: The gelatin of which the water content was 12% was filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 15 below: Material Composition: gelatin 150A: 80.3%; water: 19.7%

TABLE 15

| $T_b$ | $T_m$ | $T_e$ | $T_g$ | L/D | LFV |
|---|---|---|---|---|---|
| 110 | 120 | 140 | 140 | 66 | 810 |

EXAMPLE 13

Bone gelatin 240 bloom, grade A

A batch of gelatin with a certain content of water was prepared and conditioned and then tested in an injection molding machine. A batch of bone gelatin 240 bloom, grade A, in granulated form was conditioned as follows: The gelatin of which the water content was 10% was filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 16 below: Material Composition: gelatin 150A: 85%; water: 15%

TABLE 16

| $T_b$ | $T_m$ | $T_e$ | $T_g$ | L/D | LFV |
|---|---|---|---|---|---|
| 125 | 135 | 140 | 140 | 66 | 824 |

EXAMPLE 14

Bone gelatin 240 bloom, grade A

A batch of gelatin with a certain content of water was prepared and conditioned and then tested in an injection molding machine. A batch of bone gelatin 240 bloom, grade A, in granulated form was conditioned as follows: The gelatin of which the water content was 10% was filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 17 below: Material Composition: gelatin 240A: 81.7%; water: 18.3%

TABLE 17

| $T_b$ | $T_m$ | $T_e$ | $T_g$ | L/D | LFV |
|---|---|---|---|---|---|
| 125 | 135 | 140 | 140 | 66 | 806 |

EXAMPLE 15

Bone gelatin 150 bloom, grade B

A batch of gelatin with a certain content of water was prepared and conditioned and then tested in an injection molding machine. A batch of bone gelatin 150 bloom, grade B, in granulated form was conditioned as follows: The gelatin of which the water content was 12% was filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 18 below: Material Composition: gelatin 150B: 85%; water: 15%

TABLE 18

| $T_b$ | $T_m$ | $T_e$ | $T_g$ | L/D | LFV |
|---|---|---|---|---|---|
| 125 | 135 | 140 | 140 | 66 | 840 |

EXAMPLE 16

Bone gelatin 150 bloom, grade B

A batch of gelatin with a certain content of water was prepared and conditioned and then tested in an injection molding machine. A batch of bone gelatin 150 bloom, grade B, in granulated form was conditioned as follows: The gelatin of which the water content was 12% was filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 19 below: Material Composition: gelatin 150B: 81.7%; water: 18.3%

TABLE 19

| $T_b$ | $T_m$ | $T_e$ | $T_g$ | L/D | LFV |
|---|---|---|---|---|---|
| 110 | 130 | 130 | 130 | 66 | 835 |

EXAMPLE 17

Bone gelatin 200 bloom, grade B

A batch of gelatin with a certain content of water was prepared and conditioned and then tested in an injection molding machine. A batch of bone gelatin 200 bloom, grade B, in granulated form was conditioned as follows: The gelatin of which the water content was 10% was filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 20 below: Material Composition: gelatin 200B: 83.8%; water: 16.2%

TABLE 20

| $T_b$ | $T_m$ | $T_e$ | $T_g$ | L/D | LFV |
|---|---|---|---|---|---|
| 125 | 135 | 140 | 140 | 66 | 820 |

EXAMPLE 18

Bone gelatin 200 bloom, grade B

A batch of gelatin with a certain content of water was prepared and conditioned and then tested in an injection molding machine. A batch of bone gelatin 200 bloom, grade B, in granulated form was conditioned as follows: The gelatin of which the water content was 10% was filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 21 below: Material Composition: gelatin 200B: 82%; water: 18%

TABLE 21

| $T_b$ | $T_m$ | $T_e$ | $T_g$ | L/D | LFV |
|---|---|---|---|---|---|
| 115 | 125 | 130 | 130 | 66 | 830 |

EXAMPLE 19

Bone gelatin 150 bloom, grade B including the addition of microcrystalline cellulose A batch of gelatin with a certain content of water (and microcrystalline cellulose) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 22 below: Material Composition: microcrystalline celulose: 8%;

TABLE 22

| $T_b$ | $T_m$ | $T_e$ | $T_g$ | L/D | LFV |
|---|---|---|---|---|---|
| 125 | 130 | 140 | 140 | 66 | 1200 |

The 8% by weight of microcrystalline cellulose was added as an extender.

EXAMPLE 20

Bone gelatin 150 bloom, grade B including the addition of microfine cellulose

A batch of gelatin with a certain content of water (and microfine cellulose) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 23 below: Material Composition: microfine cellulose: 25%; gelatin 150B: 58%; water: 17%

TABLE 23

| $T_b$ | $T_m$ | $T_e$ | $T_g$ | L/D | LFV |
|---|---|---|---|---|---|
| 115 | 125 | 130 | 130 | 66 | 840 |

The 25% by weight of microfine cellulose were added as an extender.

EXAMPLE 21

Bone gelatin 150 bloom, grade B including the addition of microfine cellulose

A batch of gelatin with a certain content of water (and microfine cellulose) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 24 below: Material Composition: microfine cellulose: 8%; gelatin 150B: 70%; water: 22%

TABLE 24

| $T_b$ | $T_m$ | $T_e$ | $T_g$ | L/D | LFV |
|---|---|---|---|---|---|
| 125 | 130 | 140 | 140 | 66 | 1000 |

The 8% by weight of microfine cellulose were added as an extender.

EXAMPLE 22

Bone gelatin 150 bloom, grade B including the addition of microfine cellulose

A batch of gelatin with a certain content of water (and microfine cellulose) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 25 below: Material Composition: microfine cellulose: 25%; gelatin 150B: 59%; water: 16%

TABLE 25

| $T_b$ | $T_m$ | $T_e$ | $T_g$ | L/D | LFV |
|---|---|---|---|---|---|
| 125 | 135 | 140 | 140 | 66 | 820 |

The 8% by weight of microfine cellulose were added as an extender.

EXAMPLE 23

Bone gelatin 150 bloom, grade B including the addition of microfine cellulose

A batch of gelatin with a certain content of water (and cellulose) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 26 below: Material Composition: microfine cellulose: 9%; gelatin 150B: 76%; water: 15%

TABLE 26

| $T_b$ | $T_m$ | $T_e$ | $T_g$ | L/D | LFV |
|---|---|---|---|---|---|
| 125 | 135 | 140 | 140 | 66 | 920 |

The 9% by weight of microfine cellulose were added as an extender.

EXAMPLE 24

Bone gelatin 150 bloom, grade B including the addition of cellulose acetate phthalate A batch of gelatin with a certain content of water (and cellulose acetate phthalate) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 27 below: Material Composition: cellulose acetate phthalate: 43%; gelatin 150B: 43%; water: 14%

TABLE 27

| $T_b$ | $T_m$ | $T_e$ | $T_g$ | L/D | LFV |
|---|---|---|---|---|---|
| 125 | 135 | 140 | 140 | 66 | 760 |

The 43% by weight of cellulose acetate phthalate were added as an enteric polymer.

The resulting capsules have enteric properties (2 hours resistance in gastric juice, soluble within well 30 minutes in intestinal juice according USP XX).

EXAMPLE 25

Bone gelatin 150 bloom, grade B including the addition of cellulose acetate phthalate A batch of gelatin with a certain content of water (and cellulose acetate phthalate) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 28 below: Material Composition: cellulose acetate phthalate: 8%; gelatin 150B: 72%; water: 20%

TABLE 28

| $T_b$ | $T_m$ | $T_e$ | $T_g$ | L/D | LFV |
|---|---|---|---|---|---|
| 125 | 135 | 140 | 140 | 66 | 800 |

The 8% by weight of cellulose acetate phthalate were added as an enteric polymer.

EXAMPLE 26

A batch of HPMCP with a certain content of water (and glycerin, polyethyleneglycol and calcium-stearate) was prepared and conditioned and then tested in an injection molding machine. A batch of HPMCP in powdered form was conditioned as follows: The HPMCP of which the water content was 2% and the other additives were filled into a drum and sprayed with a specially fine spray of water to the calculated content as wanted. The batch was then thoroughly mixed and stored in a closed drum for half a day at ambient temperature. Acceptable capsules were then produced according to the working conditions listed on Table 29 below: Material Composition: HPMCP: 89%; glycerin: 6.4%; PE-glycol (10.000): 1.6%; Ca-stearate: 3%

TABLE 29

| $T_b$ | $T_m$ | $T_e$ | $T_g$ | L/D | LFV |
|---|---|---|---|---|---|
| 125 | 135 | 140 | 140 | 66 | 820 |

The 6.4% by weight of glycerin were added as a softener. The 1.6% by weight of polyethylenglycol were added as plasticizer. The 3% by weight of calcium-stearate were added as a lubricant.

The resulting capsules have enteric properties (2 hours resistance in gastric juice, soluble within well 30 minutes of intestinal juice according to USP XX).

EXAMPLE 27

Bone gelatin 150 bloom, grade B including the addition of HPMCP, glycerin, polyethylenglycol and Ca-stearate A batch of gelatin with a certain content of water (and HPMCP, glycerin, polyetheneglycol and Ca-stearate) was prepared and conditioned and then tested in an injection molding machine. A batch of bone gelatin 150 bloom, grade B, in granulated form was conditioned as follows: The gelatin of which the water content was 11.7% and the other additives were filled into a drum and sprayed with a specially fine spray of water to the calculated content as wanted. The batch was then thoroughly mixed and stored in a closed drum for half a day at ambient temperature. Acceptable capsules were then produced according to the working conditions listed on Table 30 below: Material Composition: HPMCP: 40%; glycerin:3%; PE-glycol (10,000): 1%; Ca-stearate: 1%; gelatin 150B: 45%; water: 10%

TABLE 30

| $T_b$ | $T_m$ | $T_e$ | $T_g$ | L/D | LFV |
|---|---|---|---|---|---|
| 125 | 135 | 140 | 140 | 66 | 820 |

The 3% by weight of glycerin were added as a plasticizer. The 1% by weight of polyethylenglycol were added as a plasticizer. The 1% by weight of Ca-stearate was added as a lubricant. The 40% by weight of HPMCP were added as an enteric polymer. The resulting capsules have enteric properties (2 hours resistance in gastric juice, soluble within well 30 minutes of intestinal juice according to USP XX).

EXAMPLE 28

Bone gelatin 150 bloom, grade B including the addition of HPMCP

A batch of gelatin with a certain content of water (and HPMCP) was prepared and conditioned and then tested in an injection molding machine. A batch of bone gelatin 150 bloom, grade B, in granulated form was conditioned as follows The gelatin of which the water content was 11.7% and the other additives were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 31 below: Material Composition: HPMCP: 8%; gelatin 150B: 72%, water: 20%

TABLE 31

| $T_b$ | $T_m$ | $T_e$ | $T_g$ | L/D | LFV |
|---|---|---|---|---|---|
| 118 | 125 | 130 | 130 | 66 | 1000 |

The 8% by weight of HPMCP were added as an enteric polymer.

EXAMPLE 29

Bone gelatin 150 bloom, grade B including the addition of HPMCP

A batch of acrylate with a certain content of water was prepared and conditioned and then tested in an injection molding machine. A batch of acrylate in powdered form was conditioned as follows: The acrylate of which the water content was 4% was filled into a drum and sprayed with a specially fine spray of water content as wanted. The batch was then thoroughly mixed and stored at ambient temperature. Acceptable capsules were then produced according to the working conditions listed on Table 32 below: Material Composition: acrylate: 83%; water: 17%

TABLE 32

| $T_b$ | $T_m$ | $T_e$ | $T_g$ | L/D | LFV |
|---|---|---|---|---|---|
| 120 | 140 | 140 | 140 | 66 | 850 |

The resulting capsules have enteric properties (2 hours resistance in gastric juice, soluble within well 30 minutes in intestinal juice according to USP XX).

EXAMPLE 30

Bone gelatin 150 bloom, grade B including the addition of acrylate

A batch of gelatin with a certain content of water (and acrylate) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water content as wanted. The batch was then thoroughly mixed and stored in the closed drum for half a day at ambient temperature. Acceptable gelatin capsules were then produced according to the working conditions listed on Table 33 below: Material Composition: acrylate: 25%; gelatin 150B: 59%; water: 16%

TABLE 33

| $T_b$ | $T_m$ | $T_e$ | $T_g$ | L/D | LFV |
|---|---|---|---|---|---|
| 105 | 115 | 120 | 120 | 66 | 860 |

The 25% by weight of acrylate were added as an enteric polymer.

EXAMPLE 31

Bone gelatin 150 bloom, grade B including the addition of acrylate

A batch of gelatin with a certain content of water (and acrylate) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water content as wanted. The batch was then thoroughly mixed and stored in the closed drum for half a day at ambient temperature. Acceptable gelatin capsules were then produced according to the working conditions listed on Table 34 below: Material Composition: acrylate: 8%; gelatin 150B: 76%; water: 16%

TABLE 34

| $T_b$ | $T_m$ | $T_e$ | $T_g$ | L/D | LFV |
|---|---|---|---|---|---|
| 125 | 135 | 140 | 140 | 66 | 900 |

The 8% by weight of acrylate were added as an enteric polymer.

EXAMPLE 32

Bone gelatin 150 bloom, grade B including the addition of soy protein

A batch of gelatin with a certain content of water (and soy protein) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water content as wanted. The batch was then thoroughly mixed and stored in the closed drum for half a day at ambient temperature. Acceptable gelatin capsules were then produced according to the working conditions listed on Table 35 below: Material Composition: soy protein: 39%; gelatin 150B: 39%; water: 22%

TABLE 35

| $T_b$ | $T_m$ | $T_e$ | $T_g$ | L/D | LFV |
|---|---|---|---|---|---|
| 125 | 135 | 140 | 140 | 66 | 780 |

The 39% by weight of soy protein were added as an extender.

EXAMPLE 33

Bone gelatin 150 bloom, grade B including the addition of soy protein.

A batch of gelatin with a certain content of water (and soy protein) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 36 below: Material Composition: soy protein: 8%; gelatin 150B: 76% water: 16%

TABLE 36

| $T_b$ | $T_m$ | $T_e$ | $T_g$ | L/D | LFV |
|---|---|---|---|---|---|
| 125 | 135 | 140 | 140 | 66 | 840 |

The 8% by weight of soy protein were added as an extender.

EXAMPLE 34

Bone gelatin 150 bloom, grade B including the addition of hydroxy-propyl-methyl-cellulose (HPMC)

A batch of gelatin with a certain content of water (and hydroxy-propyl-methyl-cellulose) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 37 below: Material Composition: HPMC: 44; gelatin 150B: 44; water: 12

TABLE 37

| $T_b$ | $T_m$ | $T_e$ | $T_g$ | L/D | LFV |
|---|---|---|---|---|---|
| 135 | 145 | 150 | 150 | 66 | 850 |

The 44% by weight of hydroxy-propyl-methyl-cellulose were added as an extender.

EXAMPLE 35

Bone gelatin 150 bloom, grade B including the addition of hydroxy-propyl-methyl-cellulose (HPMC)

A batch of gelatin with a certain content of water (and hydroxy-propyl-methyl-cellulose) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 38 below: Material Composition: HPMC: 8%; gelatin 150B: 75%; water: 17%

TABLE 38

| $T_b$ | $T_m$ | $T_e$ | $T_g$ | L/D | LFV |
|---|---|---|---|---|---|
| 125 | 135 | 140 | 140 | 66 | 800 |

The 8% by weight of hydroxy-propyl-methyl-cellulose were added as an extender.

EXAMPLE 36

Bone gelatin 150 bloom, grade B including the addition of Na-CMC

A batch of gelatin with a certain content of water (and Na-CMC) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 39 below: Material Composition: NA-CMC: 40%; gelatin 150B: 40% water: 20%

TABLE 39

| $T_b$ | $T_m$ | $T_e$ | $T_g$ | L/D | LFV |
|---|---|---|---|---|---|
| 125 | 135 | 140 | 140 | 66 | 840 |

The 40% by weight of Na-CMC were added as an extender.

EXAMPLE 37

Bone gelatin 150 bloom, grade B including the addition of Na-CMC

A batch of gelatin with a certain content of water (and Na-CMC) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 40 below: Material Composition: NA-CMC: 8%; gelatin 150B: 75% water: 17%

TABLE 40

| $T_b$ | $T_m$ | $T_e$ | $T_g$ | L/D | LFV |
|---|---|---|---|---|---|
| 125 | 135 | 140 | 140 | 66 | 825 |

The 8% by weight of Na-CMC were added as an extender.

EXAMPLE 38

Bone gelatin 150 bloom, grade B including the addition of polyvinylpyrrolidone

A batch of gelatin with a certain content of water (and polyvinylpyrrolidone) was prepared and conditioned and then tested in an injection molding machine.

A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 41 below: Material Composition: polyvinylpyrrolindone: 25%; gelatin 150B: 60%; water: 15%

TABLE 41

| $T_b$ | $T_m$ | $T_e$ | $T_g$ | L/D | LFV |
|---|---|---|---|---|---|
| 125 | 135 | 140 | 140 | 66 | 820 |

The 25% by weight of polyvinylpyrrolidone were added as an extender.

EXAMPLE 39

Bone gelatin 150 bloom, grade B including the addition of polyvinylpyrrolidone

A batch of gelatin with a certain content of water (and polyvinylpyrrolidone) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 42 below: Material Composition: polyvinylpyrrolindone: 9%; gelatin 150B: 77%; water: 14%

TABLE 42

| $T_b$ | $T_m$ | $T_e$ | $T_g$ | L/D | LFV |
|---|---|---|---|---|---|
| 125 | 135 | 140 | 140 | 66 | 860 |

The 9% by weight of polyvinylpyrrolidone were added as an extender.

EXAMPLE 40

A batch of agar with a certain content of water was prepared and then tested in an injection molding machine. A batch of bone agar in powdered form was conditioned as follows: The agar of which the water content was 16% was filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 43 below: Material Composition: agar: 75%; water: 25%

TABLE 43

| $T_b$ | $T_m$ | $T_e$ | $T_g$ | L/D | LFV |
|---|---|---|---|---|---|
| 110 | 120 | 130 | 130 | 66 | 1240 |

EXAMPLE 41

Bone gelatin 150 bloom, grade B including the addition of agar

A batch of gelatin with a certain content of water (and agar) was prepared and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 44 below: Material Composition: agar: 38%; gelatin 150B: 38%; water: 24%

TABLE 44

| $T_b$ | $T_m$ | $T_e$ | $T_g$ | L/D | LFV |
|---|---|---|---|---|---|
| 110 | 120 | 130 | 130 | 66 | 820 |

The 38% by weight of agar were added as extender.

EXAMPLE 42

Bone gelatin 150 bloom, grade B including the addition of agar

A batch of gelatin with a certain content of water (and agar) was prepared and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 45 below: Material Composition: agar: 8%; gelatin 150B: 73%; water: 19%

TABLE 45

| $T_b$ | $T_m$ | $T_e$ | $T_g$ | L/D | LFV |
|---|---|---|---|---|---|
| 110 | 120 | 130 | 130 | 66 | 820 |

The 8% by weight of agar were added as extender.

EXAMPLE 42a

Bone gelatin 150 bloom, grade B including the addition of agar

A batch of gelatin with a certain content of water (and agar) was prepared and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 45 below: Material Composition: agar: 8%; gelatin 150B: 73%; water: 19%

TABLE 45a

| $T_b$ | $T_m$ | $T_e$ | $T_g$ | L/D | LFV |
|---|---|---|---|---|---|
| 110 | 120 | 130 | 130 | 66 | 850 |

The 8% by weight of agar were added as extender.

EXAMPLE 43

Bone gelatin 150 bloom, grade B including the addition of dextran

A batch of gelatin with a certain content of water (and dextran) was prepared and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 46 below: Material Composition: dextran: 24%;, gelatin 150B: 57%; water: 19%

TABLE 46

| $T_b$ | $T_m$ | $T_e$ | $T_g$ | L/D | LFV |
|---|---|---|---|---|---|
| 125 | 135 | 140 | 140 | 66 | 820 |

The 24% by weight of dextran were added as extender.

EXAMPLE 44

Bone gelatin 150 grade B including the addition of dextran

A batch of gelatin with a certain content of water (and dextran) was prepared and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 47 below: Material Composition: dextran: 9%; gelatin 150B: 77%; water: 14%

TABLE 47

| $T_b$ | $T_m$ | $T_e$ | $T_g$ | L/D | LFV |
|---|---|---|---|---|---|
| 125 | 135 | 140 | 140 | 66 | 840 |

The 9% by weight of dextran were added as extender.

EXAMPLE 45

Bone gelatin 150 bloom, grade B including the addition of alginate

A batch of gelatin with a certain content of water (and alginate) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 48 below: Material Composition: alginate: 41%; gelatin 150B: 41% water: 18%

TABLE 48

| $T_b$ | $T_m$ | $T_e$ | $T_g$ | L/D | LFV |
|---|---|---|---|---|---|
| 110 | 120 | 140 | 140 | 66 | 850 |

The 41% by weight of alginate were added as extender.

EXAMPLE 46

Bone gelatin 150 bloom, grade B including the addition of alginate

A batch of gelatin with a certain content of water (and alginate) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 49 below: Material Composition: alginate: 8%; gelatin 150B: 74% water: 18%

TABLE 49

| $T_b$ | $T_m$ | $T_e$ | $T_g$ | L/D | LFV |
|---|---|---|---|---|---|
| 110 | 120 | 140 | 140 | 66 | 840 |

The 8% by weight of alginate were added as extender.

EXAMPLE 47

Bone gelatin 150 bloom, grade B including the addition of algin

A batch of gelatin with a certain content of water (and algin) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 50 below: Material Composition: algin: 41%; gelatin 150B: 41%; water: 18%

TABLE 50

| $T_b$ | $T_m$ | $T_e$ | $T_g$ | L/D | LFV |
|---|---|---|---|---|---|
| 100 | 120 | 120 | 120 | 66 | 850 |

The 41% by weight of algin were added as extender.

EXAMPLE 48

Bone gelatin 150 bloom, grade B including the addition of algin

A batch of gelatin with a certain content of water (and algin) was prepared and conditioned and then tested in an injection molding machine. A batch of bone gelatin 150 bloom, grade B, in granulated form was conditioned as follows: The gelatin of which the water content was 11.7% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 51 below: Material Composition: algin: 8%; gelatin 150B: 74% water: 18%

TABLE 51

| $T_b$ | $T_m$ | $T_e$ | $T_g$ | L/D | LFV |
|---|---|---|---|---|---|
| 100 | 120 | 120 | 120 | 66 | 834 |

The 8% by weight of algin were added as extender.

EXAMPLE 49

A batch of HPMCP with a certain content of water (and glycerin, polyethlenglycol, calcium-stearate and microfine cellulose) was prepared and conditioned and then tested in an injection molding machine. A batch of HPMCP in powdered form was conditioned as follows: The HPMCP of which the water content was 2% and the other additive were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 52 below: Material Composition: HPMCP: 57.4%; glycerin: 4.1%; PE-glycol (10.000): 1%; Ca-stearate: 2%; microfine cellulose: 27.6%; water: 7.9%

TABLE 52

| $T_b$ | $T_m$ | $T_e$ | $T_g$ | L/D | LFV |
|---|---|---|---|---|---|
| 110 | 120 | 140 | 140 | 66 | 835 |

The 4.1% by weight of glycerin were added as a softener. The 1% by weight of polyethylenglycol was added as a plasticizer. The 2% by weight of calcium-stearate were added as a lubricant. The 27.6% by weight of microfine cellulose were added as an extender.

The resulting capsules have enteric properties (2 hours resistance in gastric juice, soluble within well 30 minutes in intestinal juice according to USP XX).

EXAMPLE 50

A batch of HPMCP with a certain content of water (and glycerin, polyethlenglycol, calcium-stearate and microfine cellulose) was prepared and conditioned and then tested in an injection molding machine. A batch of HPMCP in powdered form was conditioned as follows: The HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 53 below: Material Composition: HPMCP: 74.9%; glycerin: 5.4%; PE-glycol (10.000): 1.3%; Ca-stearate: 2.5%; microfine cellulose: 9.4%; water: 6.5%

TABLE 53

| $T_b$ | $T_m$ | $T_e$ | $T_g$ | L/D | LFV |
|---|---|---|---|---|---|
| 110 | 120 | 140 | 140 | 66 | 880 |

The 5.4% by weight of glycerin were added as a softener. The 1.3% by weight of polyethylenglycol were added as a plasticizer. The 2.5% by weight of calcium-stearate were added as a lubricant. The 9.4% by weight of microfine cellulose were added as an extender.

The resulting capsules have enteric properties (2 hours resistance in gastric juice, soluble within well 30 minutes in intestinal juice according to USP XX).

EXAMPLE 51

A batch of HPMCP with a certain content of water (and glycerin, polyethylenglycol, calcium-stearate and Na-CMC) was prepared and conditioned and then tested in an injection molding machine. A batch of HPMCP in powdered form was conditioned as follows: The HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 54 below: Material Composition: HPMCP: 74.7%; glycerin: 5.4%; PE-glycol (10.000): 1.3%; Ca-stearate: 2.5%; Na-CMC: 9.4%; water: 6.7%

TABLE 54

| $T_b$ | $T_m$ | $T_e$ | $T_g$ | L/D | LFV |
|---|---|---|---|---|---|
| 110 | 120 | 140 | 140 | 66 | 850 |

The 5.4% by weight of glycerin were added as a softener. The 1.3% by weight of polyethylenglycol were added as a plasticizer. The 2.5% by weight of calcium-stearate were added as a lubricant. The 9.4% by weight of Na-CMC were added as an extender. The resulting capsules have enteric properties (2 hours resistance in gastric juice, soluble within well 30 minutes in intestinal juice according to USP XX).

EXAMPLE 52

A batch of HPMCP with a certain content of water (and glycerin, polyethlenglycol, calcium-stearate and agar) was prepared and conditioned and then tested in an injection molding machine. A batch of HPMCP in powdered form was conditioned as follows: The HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 55 below: Material Composition: HPMCP: 37.4%; glycerin: 2.7%; PE-glycol (10.000): 0.7%; Ca-stearate: 1.3%; agar: 42%; water: 15.9%

TABLE 55

| $T_b$ | $T_m$ | $T_e$ | $T_g$ | L/D | LFV |
|---|---|---|---|---|---|
| 110 | 120 | 130 | 130 | 66 | 830 |

The 2.7% by weight of glycerin were added as a softener. The 0.7% by weight of polyethylenglycol were added as a plasticizer. The 1.3% by weight of calcium-stearate were added as a lubricant. The 42% by weight of agar were added as an extender. The 9.4% by weight of Na-CMC were added as an extender. The resulting capsules have enteric properties (2 hours resistance in gastric juice, soluble within well 30 minutes in intestinal juice according to USP XX).

EXAMPLE 53

A batch of HPMCP with a certain content of water (and glycerin, polyethlenglycol, calcium-stearate and agar) was prepared and conditioned and then tested in an injection molding machine. A batch of HPMCP in powdered form was conditioned as follows: The HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 56 below: Material Composition: HPMCP: 69%; glycerin: 5%; PE-glycol (10.000): 1.2%; Ca-stearate: 2.3%; agar: 8.7%; water: 13.8%

TABLE 56

| $T_b$ | $T_m$ | $T_e$ | $T_g$ | L/D | LFV |
|---|---|---|---|---|---|
| 110 | 125 | 135 | 135 | 66 | 830 |

The 5% by weight of glycerin were added as a softener. The 1.2% by weight of polyethylenglycol were added as a plasticizer. The 2.3% by weight of calcium-stearate were added as a lubricant. The 8.7% by weight of agar were added as an extender. The resulting capsules have enteric properties (2 hours resistance in gastric juice, soluble within well 30 minutes in intestinal juice according to USP XX).

EXAMPLE 54

A batch of HPMCP with a certain content of water (and glycerin, polyethlenglycol, calcium-stearate and hydroxypropylmethyl-cellulose) was prepared and conditioned and then tested in an injection molding machine. A batch of HPMCP in powdered form was conditioned as follows: The HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 57 below: Material Composition: HPMCP: 39.9%; glycerin: 2.9%; PE-glycol (10.000): 0.7%; Ca-stearate: 1.3%; HPMC: 44.9%; water: 10.3%

TABLE 57

| $T_b$ | $T_m$ | $T_e$ | $T_g$ | L/D | LFV |
|---|---|---|---|---|---|
| 110 | 120 | 140 | 140 | 66 | 835 |

The 2.9% by weight of glycerin were added as a softener. The 0.7% by weight of polyethylenglycol were added as a plasticizer. The 1.3% by weight of calcium-stearate were added as a lubricant. The 44.9% by weight of hydroxypropylmethyl-cellulose were added as an extender.

The resulting capsules have enteric properties (2 hours resistance in gastric juice, soluble within well 30 minutes in intestinal juice according to USP XX).

EXAMPLE 55

A batch of HPMCP with a certain content of water (and glycerin, polyethylenglycol, calcium-stearate and hydroxypropylmethyl-cellulose) was prepared and conditioned and then tested in an injection molding machine. A batch of HPMCP in powdered form was conditioned as follows: The HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 58 below: Material Composition: HPMCP: 73.9%; glycerin: 5.3%; PE-glycol (10.000): 1.3%; Ca-stearate: 2.5%; HPMC: 9.2%; water: 7.8%

TABLE 58

| $T_b$ | $T_m$ | $T_e$ | $T_g$ | L/D | LFV |
|---|---|---|---|---|---|
| 110 | 125 | 135 | 135 | 66 | 860 |

The 5.3% by weight of glycerin were added as a softener. The 1.3% by weight of polyethylenglycol were added as a plasticizer. The 2.5% by weight of calcium-stearate were added as a lubricant. The 9.2% by weight of hydroxypropylmethyl-cellulose were added as an extender.

The resulting capsules have enteric properties (2 hours resistance in gastric juice, soluble within well 30 minutes in intestinal juice according to USP XX).

EXAMPLE 56

A batch of HPMCP with a certain content of water (and glycerin, polyethylenglycol, calcium-stearate and soy protein) was prepared and conditioned and then tested in an injection molding machine. A batch of HPMCP in powdered form was conditioned as follows: The HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 59 below: Material Composition: HPMCP: 40%; glycerin: 2.9%; PE-glycol (10.000): 0.7%; Ca-stearate: 1.3%; soy protein: 44.9%; water: 10.2%

TABLE 59

| $T_b$ | $T_m$ | $T_e$ | $T_g$ | L/D | LFV |
|---|---|---|---|---|---|
| 110 | 120 | 140 | 140 | 66 | 840 |

The 2.9% by weight of glycerin were added as a softener. The 0.7% by weight of polyethylenglycol were added as a plasticizer. The 1.3% by weight of calcium-stearate were added as a lubricant. The 44.9% by weight of soy protein were added as an extender.

The resulting capsules have enteric properties (2 hours resistance in gastric juice, soluble within well 30 minutes in intestinal juice according to USP XX).

EXAMPLE 57

A batch of HPMCP with a certain content of water (and glycerin, polyethylenglycol, calcium-stearate and soy protein) was prepared and conditioned and then tested in an injection molding machine. A batch of HPMCP in powdered form was conditioned as follows: The HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 60 below: Material Composition: HPMCP: 74.3%; glycerin: 5.3%; PE-glycol (10.000): 1.3%; Ca-stearate: 2.5%; soy protein: 9.4%; water: 7.2%

TABLE 60

| $T_b$ | $T_m$ | $T_e$ | $T_g$ | L/D | LFV |
|---|---|---|---|---|---|
| 110 | 125 | 135 | 135 | 66 | 1400 |

The 5.3% by weight of glycerin were added as a softener. The 1.3% by weight of polyethylenglycol were added as a plasticizer. The 2.5% by weight of calcium-stearate were added as a lubricant. The 9.4% by weight of soy protein were added as an extender.

The resulting capsules have enteric properties (2 hours resistance in gastric juice, soluble within well 30 minutes in intestinal juice according to USP XX).

EXAMPLE 58

A batch of HPMCP with a certain content of water (and glycerin, polyethylenglycol, calcium-stearate and polyvinylpyrrolidone) was prepared and conditioned and then tested in an injection molding machine. A batch of HPMCP in powdered form was conditioned as follows: The HPMCP of which the water content was 2% and the other additives were filled into a drum and sprayed with a specially fine spray of water to the calculated content as wanted. The batch was then thoroughly mixed and stored in the closed drum for half a day at ambient temperature.

Acceptable gelatin capsules were then produced according to the working conditions listed on Table 61 below: Material Composition: HPMCP: 38.7%; glycerin: 2.8%; PE-glycol (10.000): 0.7%; Ca-stearate: 1.3%; polyvinylpyrrolidone: 43.5%; water: 13.0%

TABLE 61

| $T_b$ | $T_m$ | $T_e$ | $T_g$ | L/D | LFV |
|---|---|---|---|---|---|
| 120 | 140 | 140 | 140 | 66 | 830 |

The 2.8% by weight of glycerin were added as a softener. The 0.7% by weight of polyethylenglycol were added as a plasticizer. The 1.3% by weight of calcium-stearate were added as a lubricant. The 43.5% by weight of polyvinylpyrrolidone were added as an extender.

The resulting capsules have enteric properties (2 hours resistance in gastric juice, soluble within well 30 minutes in intestinal juice according to USP XX).

EXAMPLE 59

Bone gelatin 150 bloom, grade B including the addition of crosslinking agent

A batch of gelatin with a certain content of water was prepared and conditioned and then tested in an injection molding machine. A batch of bone gelatin 150 bloom, grade B, in granulated form was conditioned as follows: The content of which the water content was 11.7% was filled into a drum and sprayed with a specially fine spray of water to the calculated content as wanted. The batch was then thoroughly mixed and stored in the closed drum for half a day at ambient temperature. Acceptable gelatin capsules were then produced as follows: Glutaraldehyde and formaldehyde have been used as crosslinking agent whereby this substance has been added to the molten gelatin in the sprue just at the gate. In order get a homogeneous mixture of crosslinking agent and gelatin, the sprue has been equipped with a mixing device. The following material compositions were tested:

TABLE 62

| Material Composition in % by weight | Working Conditions | | | | | |
|---|---|---|---|---|---|---|
|  | $T_b$ | $T_m$ | $T_e$ | $T_g$ | L/D | LFV |
| Gelatin 150B: 82.6; glutaraldehyde: 0.4; water: 17 | 110 | 120 | 140 | 140 | 66 | 860 |
| Gelatin 150B: 82.96; glutaraldehyde: 0.04; water: 17 | 110 | 120 | 140 | 140 | 66 | 860 |
| Gelatin 150B: 82.90; glutaraldeyhyde: 0.1; water: 17 | 110 | 120 | 140 | 140 | 66 | 860 |

These capsules were soluble in water of 37° C. during at least 2 hours.

EXAMPLE 60

Bone gelatin 150 bloom, grade B including the addition of hydroxypropyl cellulose A batch of gelatin with a certain content of water (and hydroxypropyl cellulose) was prepared and conditioned and then tested in an injection molding machine. A batch of bone gelatin 150 bloom, grade B, in granulated form was conditioned as follows: The gelatin of which the water content was 17% and the other additive were filled into a drum and sprayed with a specially fine spray of water to be calculated content as wanted. The batch was then thoroughly mixed and stored in the closed drum for half a day at ambient temperature. Acceptable gelatin capsules were then produced according to the working conditions listed on Table 63 below: Material Composition: Hydroxypropyl cellulose: 17%; gelatin 150B: 68%; water: 17%

TABLE 63

| $T_b$ | $T_m$ | $T_e$ | $T_g$ | L/D | LFV |
|---|---|---|---|---|---|
| 100 | 120 | 130 | 130 | 66 | 1000 |

The 17% by weight of hydroxypropyl cellulose were added as a extender.

EXAMPLE 61

A batch of gum arabic with a certain content of water was prepared and conditioned and then tested in an injection molding machine. The batch of gum arabic in powdered form was conditioned as follows: The gum arabic of which the water content was 10.8% was filled into a drum and sprayed with a specially fine spray of water to the calculated content as wanted. The batch was then thoroughly mixed and stored in the closed drum for half a day at ambient temperature. Acceptable capsules were then produced according to the working conditions listed on Table 64 below: Material Composition: gum arabic: 80.9%; water: 19.1%

TABLE 64

| $T_b$ | $T_m$ | $T_e$ | $T_g$ | L/D | LFV |
|---|---|---|---|---|---|
| 75 | 105 | 112 | 130 | 66 | 800 |

EXAMPLE 62

A batch of methylcellulose with a certain content of water was prepared and conditioned and then tested in an injection molding machine. The batch of methylcellulose in powdered form was conditioned as follows: The methylcellulose of which the water content was 6.6% was filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 65 below: Material Composition: methylcellulose: 81.2%; water: 18.8%

TABLE 65

| $T_b$ | $T_m$ | $T_e$ | $T_g$ | L/D | LFV |
|---|---|---|---|---|---|
| 84 | 129 | 149 | 161 | 66 | 800 |

EXAMPLE 63

A batch of polyvinylpyrrolidone with a certain content of water was prepared and then tested in an injection molding machine. The batch of polyvinylpyrrolidone in powdered form was conditioned as follows: The polyvinylpyrrolidone of which the water content was 16.8% was filled into a drum and sprayed with a specially fine spray of water to the calculated content as wanted. The batch was then thoroughly mixed and stored in the closed drum for half a day at ambient temperature. Acceptable capsules were then produced according to the working conditions listed on Table 66 below: Material Composition: polyvinylpyrrolidone: 81%; water: 19%

TABLE 66

| $T_b$ | $T_m$ | $T_e$ | $T_g$ | L/D | LFV |
|---|---|---|---|---|---|
| 85 | 130 | 135 | 135 | 66 | 800 |

EXAMPLE 64

A batch of cellulose acetate phthalate with a certain content of water was prepared and then tested in an injection molding machine. The batch of cellulose acetate phthalatein powdered form was conditioned as follows: The cellulose acetate phthalate of which the water content was 5.1% was filled into a drum and sprayed with a specially fine spray of water to the calculated content as wanted. The batch was then thoroughly mixed and stored in the closed drum for half a day at ambient temperature. Acceptable capsules were then produced according to the working conditions listed on Table 67 below: Material Composition: cellulose acetate phthalate: 81%; water: 19%

TABLE 67

| $T_b$ | $T_m$ | $T_e$ | $T_g$ | L/D | LFV |
|---|---|---|---|---|---|
| 90 | 130 | 140 | 145 | 66 | 800 |

As can be seen from the examples, bone gelatins identified as 80A; 150A; 240A; 150B and 200B were used in connection with certain of the examples following Example 9. The identification "A" indicates that the gelatin was produced by acid processing of collagen raw materials, and the identification "B" indicates that the gelatin was obtained by alkaline processing of collagen raw materials. The numerical values are "bloom" values. A high bloom value indicates that the gelatin polymer has only been degraded slightly whereas low bloom values indicate that the polymer has been extensively degraded. There is a rough, but not absolute, correlation between bloom values and molecular weight, i.e., the higher bloom values indicate higher molecular weight and the lower bloom vaues indicate lower molecular weight gelatins.

The molecular weight values for the examples after Example 9 utilizing gelatins are as follows:

Example 10, bone gelatin, 80 bloom, grade A

The following specifications of the molecular weight distribution have been measured:

| Weight (Average) | 81,000 Dalton |
|---|---|
| Viscosity (Average) | 64,000 Dalton |
| Molecular mass of smallest molecules | 10,000 Dalton |
| Molecular mass of largest molecules | 15,300,000 Dalton |

Examples 13–14, bone gelatin 240 bloom, grade A

The following specifications of the molecular weight distribution have been measured:

| Weight (Average) | 221,000 Dalton |
|---|---|
| Viscosity (Average) | 188,000 Dalton |
| Molecular mass of smallest molecules | 10,000 Dalton |
| Molecular mass of largest molecules | 15,300,000 Dalton |

Examples 15–16, 19–25, 27–28, 30–39, 41–48, 59, bone gelatin 150 bloom, grade B

The following specifications of the molecular weight distribution have been measured:

| Weight (Average) | 258,000 Dalton |
|---|---|
| Viscosity (Average) | 155,000 Dalton |
| Molecular mass of smallest molecules | 10,000 Dalton |
| Molecular mass of largest molecules | 15,300,000 Dalton |

Examples 17–18, bone gelatin 200 bloom, grade B

The following specifications of the molecular weight distribution have been measured:

| Weight (Average) | 299,000 Dalton |
|---|---|
| Viscosity (Average) | 187,000 Dalton |
| Molecular mass of smallest molecules | 10,000 Dalton |
| Molecular mass of largest molecules | 15,300,000 Dalton |

In addition to the foregoing compositions, injection moldable compositions in accordance with this invention have been made which included magnesium stearate at a concentration of 0.5% and at a concentration of 10% based on the weight of the entire composition. Injection moldable compositions in accordance with this invention have also been made which contain talc at 0.5% and at 10% concentrations based on the weight of the entire composition.

As can be seen from the foregoing examples, the following compounds have been used. Descriptions for these compounds are as set forth below.

Example 19, microcrystalline cellulose

The microcrystalline cellulose used was AVICEL PH 102 obtainable from FMC Corp., Marcus Hook, PA. Other types of microcrystalline cellulose could be used, such as AVICEL PH 105 or 101, both from FMC Corp.

Examples 20-23, 49, 50 microfine cellulose

The microfine cellulose used was ELCEMA G250 by Degussa, Frankfurt and SOLKA FLOC Five granular, lot 1-4-20x. Other types and brands of microfine cellulose could be used such as ELCEMA P050, P100, or F150, also obtainable from Degussa.

Examples 24, 25, 64, cellulose acetate phthalate (CAP)

The cellulose acetate phthalate used contained 30-40% phthalate groups, 17-23% acetate groups, and about 6% free acid groups. A suitable commercial product for use in these examples is obtainable from Eastman Kodak Co., Rochester, N.Y.

Examples 26, 27, 49-58, polyethylene glycol (PEG)

PEG of a molecular weight of 10,000 was used. However other PEG's can be used, preferably with a molecular weight greater than 1,000. Commercial brands of PEG suitable for use in these examples include but are not limited to: CARBOWAX by Union Carbide, NY, PLUROCOL by Wyandotte, Michigan, POLYGLYCOL by Dow Chemical, Michigan, POLYGLYKOL E by Hoechst, Frankfurt, POLYWACHS by Huls, Marl, TETRONIC by Kuhlman, Paris, and LANOGEN by Hoechst, Frankfurt.

Examples 26-28, 49-58, hydroxypropylmethyl cellulose phthalate (HPMCP)

The HPMCP used had a molecular weight of 20,000. A suitable commercial brand for use in these examples is HPMCP HP 50 obtained from Shinetsu Chemical Co., Tokyo.

Examples 29-31, acrylate

Acrylate is a copolymer of acrylic acid and acid ethylester. The acrylate used had an acid number of 315 mg KOH/g and was obtained as EUDRAGIT L from Rohm Pharma GmbH, Darmstadt.

Examples 32, 33, 56, 57, soy protein

The soy protein used was of normal food grade and is obtainable as PURINA PROTEINS from Ralston Purina, Missouri.

Examples 34, 35, 54, 55, hydroxypropylmethyl cellulose (HPMC)

The HPMC used contained 19-30% methoxy, 3-12% hydroxypropyl groups and had a molecular weight of 6000. It is obtainable as VISCONTRAN from Henkel, Dusseldorf.

Examples 36, 37, 51, sodium carboxymethyl cellulose (Na-CMC)

The Na-CMC used had an average molecular weight of 250,000 with a degree of substitution of 0.7. It was obtained as HERCULES CMC from Hercules Powder Co., Delaware.

Examples 38, 39, 58, 63, polyvinylpyrrolidone (PVP)

The PVP used had a pH of 3.5-5.0 in a 1% solution and had an average molecular weight of 10,000. It is obtainable as KOLLIDON from BASF AG, Ludwigshafen.

Examples 40-42a, 52, 53, agar

The macromolecule probably consists of the alternating copolymers $\beta$-D-galactopyranosyl-and 3,6-Anhydro-$\beta$-L-galactopyranosyl-residue linked in the (1,3) position. The agar-agar used is of normal food grade, 60-80 mesh size.

Examples 43, 44, dextran

Dextran consists of poly($\alpha$-(1,6)-D-glucose) with many $\alpha$-1,4 branches. Average molecular weight is 110,000 Daltons.

Examples 45, 46, alginate

Alginate is produced from seaweed and is a sodium salt. The product used was obtained from Proton & Fagertum AS, Norway.

Examples 47, 48, algin

Algin is the free acid counterpart of alginate (described above for examples 45 and 46).

Example 60, hydroxypropyl cellulose (HPC)

The HPC used had an average molecular weight of 900,000 to 1,000,000, with a degree of substitution between 2 and 3. It is commercially available as KLUCEL HF from Hercules Inc., Wilmington. KLUCEL LF, also from Hercules, is suitable for use in these examples as well.

Example 61, gum arabic

The principal chain of the gum arabic polysaccharide consists essentially of 1,3 D-galactopyranose units. The gum arabic used had an average molecular weight of between 200,000 and 300,000.

Example 62, methyl cellulose

The methyl cellulose used had a degree of substitution of approximately 2. It is obtained as VISCONTRAN MC 400 from Henkel, Dusseldorf.

While there have now been described and illustrated several embodiments of the present invention, the scope and working range of the present invention shall not be limited by the examples given above. The invention comprises as well various changes and modifications which will occur to those skilled in the art.

It is intended in the appended claims to cover all such changes and modifications as fall within the true spirit and scope of the present invention.

What is claimed is:

1. A molded hydrophilic gelatin-water containing shaped article of manufacture wherein the water content is in the range of from about 5% to about 25% by weight of the hydrophilic gelatin, said shaped article being formed directly:
- (a) from a hydrophilic gelatin-water solution at temperature in the range of from 50° C. to about 190° C. and elevated pressures, wherein the water content was maintained in the range of about 5 to 25% by weight of the hydrophilic gelatin;
- (b) by reducing the temperature of said hydrophilic gelatin-water solution during molding to below the glass transition temperature of said hydrophilic gelatin; whereby said molded article exhibits a self sustaining shape and negligible reversible elastic deformation of the hydrophilic gelatin.

2. A capsule capable of being self sustaining, having as its basic structural component a material which is in the form of a hydrophilic gelatin having its microstructure defined by said gelatin having been subjected to temperatures beyond it glass transition point and its melting point prior to shaping by injection molding.

3. The article or capsule of claims 1 or 2 wherein the gelatins have (a) a molecular mass of 10,000 to 2,000,000 dalatons and (b) molecular mass ranges of 10,000 to 2,000,000 and 10,000,000 to 20,000,000 daltons.

4. The article or capsule of claim 3 wherein the water is present and maintained at a predetermined amount in the range of about 10 to about 20% by weight of the gelatin.

5. The composition of claim 3 wherein extenders are present, said extenders being selected from the group consisting of vegetable proteins including sunflower proteins, soybean proteins, cotton seed proteins, peanut proteins, rape seed proteins; lactose; gum arabic; acrylates; methacrylates; cellulose and water soluble derivatives of cellulose including hydroxyethylcellulose, cellulose acetate phthalate (CAP), hydroxypropyl cellulose, hydroxypropyl methylcellulose, hydroxypropyl methylcellulose phthalate (HPMCP), methylcellulose, sodium carboxymethyl cellulose, hydroxymethyl cellulose; acryic acid polymers; polyvinylpyrrolidone; shellac; bentonite; vinylacetate polymers; polyvinylacetatephthalate; phtalated gelatin; succinated gelatin; crotonic acid polymers; and polysaccharides incluing agar-agar.

6. The article or capsule of claims 1 or 2 wherein extenders are present, said extenders being selected from the group consisting of vegetable proteins including sunflower proteins, soybean proteins, cotton seed proteins, peanut proteins, rape seed proteins, blood proteins, egg proteins, and acetylated derivatives thereo, alginates, lactose, gum arabic, cellulose and water soluble derivatives of cellulose including hydroxyethylcellulose, hydroxypropylcellulose, hydroxypropylmethylcellulose, hydroxymethylcellulose, acrylic acid polymers, polyvinylpyrrolidone, bentonite, vinylacetate polymers, agar-agar and other water soluble polysaccharides.

7. The capsule of claim 2 wherein the capsule parts are subjected to minimal deformation during forming.

8. The article or capsule of claims 1 or 2 wherein a crosslinking agent is added just prior to pressure molding.

9. The article or capsule of claims 1 or 2 wherein a plasticizing agent is present.

10. The article or capsule of claims 1 or 2 wherein a lubricating agent is present.

11. The article or capsule of claims 1 or 2 wherein a coloring agent is present.

12. The article of claim 1 wherein the water is present in the amount of about 10 to about 20% by weight of the gelatin.

13. An injection molded hydrophilic gelatin water containing shaped artile of manufacture wherein said article as ejected from the mold has a water content in the range of from about 5% to about 25% by weight of the hydrophilic gelatin and exhibits an essentially amorphous gelatin structure.

14. The article of claim 13 wherein the hydrophilic gelatin is a gelatin selected from those gelatins which have (a) a molecular mass of 10,000 to 2,000,000 daltons and (b) molecular mass ranges of 10,000 to 2,000,000 and 10,000,000 to 20,000,000 daltons.

15. Thee article of claim 14 wherein the water is present in the amount of about 10 to about 20% by weight of the gelatin.

16. The capsule according to claim 2 wherein the moisture content is between 5 and 25% as the polymer was heated past the melting and glass transition points.

17. A hydrophilic gelatin water composition having no phase separation of the water from the hydrophilic gelatin water mixture at a water content of between about 5 and 25% by weight of the hydrophilic gelatin, said mixture being obtained by:
- (a) mixing the gelatin with water in a predetermined amount between about 5 and 25% by weight of the hydrophilic gelatin;
- (b) heating the hydrophilic gelatin with said water while maintaining said predetermined water content to form a melt;
- (c) further heating the hydrophilic gelatin and water above its glass transition temperature and above its melting point to dissolve the melt in the water and achieve a melt as a molecularly dispersed solution.

* * * * *